(12) United States Patent
Jones et al.

(10) Patent No.: US 11,813,261 B2
(45) Date of Patent: Nov. 14, 2023

(54) HDAC INHIBITORS, ALONE OR IN COMBINATION WITH BTK INHIBITORS, FOR TREATING CHRONIC LYMPHOCYTIC LEUKEMIA

(71) Applicants: ACETYLON PHARMACEUTICALS, INC., Summit, NJ (US); H. LEE MOFFITT CANCER CENTER AND RESEARCH INSTITUTE, INC., Tampa, FL (US)

(72) Inventors: Simon S. Jones, Harvard, MA (US); Steven N. Quayle, Brookline, MA (US); Eva Sahakian, Tampa, FL (US); Javier Pinilla Ibarz, Tampa, FL (US)

(73) Assignees: ACETYLON PHARMACEUTICALS, INC., Summit, NJ (US); H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 16/093,278

(22) PCT Filed: Apr. 19, 2017

(86) PCT No.: PCT/US2017/028435
§ 371 (c)(1),
(2) Date: Oct. 12, 2018

(87) PCT Pub. No.: WO2017/184774
PCT Pub. Date: Oct. 26, 2017

(65) Prior Publication Data
US 2019/0209559 A1    Jul. 11, 2019

Related U.S. Application Data

(60) Provisional application No. 62/324,733, filed on Apr. 19, 2016.

(51) Int. Cl.
| | | |
|---|---|---|
| *A61K 31/505* | (2006.01) | |
| *A61K 31/519* | (2006.01) | |
| *C07D 239/42* | (2006.01) | |
| *A61K 45/06* | (2006.01) | |
| *A61P 35/00* | (2006.01) | |

(52) U.S. Cl.
CPC .......... *A61K 31/505* (2013.01); *A61K 31/519* (2013.01); *A61K 45/06* (2013.01); *A61P 35/00* (2018.01); *C07D 239/42* (2013.01); *A61K 2300/00* (2013.01)

(58) Field of Classification Search
CPC ................................................... A61K 31/505
USPC .................................................... 514/262.1
See application file for complete search history.

(56) References Cited

U.S. PATENT DOCUMENTS

| | | |
|---|---|---|
| 3,549,633 A | 12/1970 | Grabowski et al. |
| 6,777,217 B1 | 8/2004 | Schreiber et al. |
| 7,244,853 B2 | 7/2007 | Schreiber et al. |
| 7,250,504 B2 | 7/2007 | Grozinger et al. |
| 7,994,362 B2 | 8/2011 | Schreiber et al. |
| 8,088,781 B2 | 1/2012 | Honigberg et al. |
| 8,148,526 B1 | 4/2012 | van Duzer et al. |
| 8,394,810 B2 | 3/2013 | van Duzer et al. |
| 8,609,678 B2 | 12/2013 | van Duzer et al. |
| 8,614,223 B2 | 12/2013 | van Duzer et al. |
| 9,145,412 B2 | 9/2015 | van Duzer et al. |
| 2004/0266769 A1 | 12/2004 | Bressi et al. |
| 2005/0119305 A1 | 6/2005 | Naka et al. |
| 2006/0239909 A1 | 10/2006 | Anderson et al. |
| 2007/0093413 A1 | 4/2007 | Schreiber et al. |
| 2007/0149495 A1 | 6/2007 | Bressi et al. |
| 2008/0207590 A1 | 8/2008 | Deziel et al. |
| 2009/0023786 A1 | 1/2009 | Miller et al. |
| 2009/0181987 A1 | 7/2009 | Honigberg et al. |
| 2009/0209590 A1 | 8/2009 | Mazitschek et al. |
| 2009/0305384 A1 | 12/2009 | Grozinger et al. |
| 2009/0312363 A1 | 12/2009 | Bradner et al. |
| 2010/0137196 A1 | 6/2010 | Schreiber et al. |
| 2010/0152254 A1 | 6/2010 | Bialer et al. |
| 2010/0168463 A1 | 7/2010 | Hirata et al. |

(Continued)

FOREIGN PATENT DOCUMENTS

| | | |
|---|---|---|
| EP | 2524918 A1 | 11/2012 |
| JP | 2016-536354 A | 11/2016 |

(Continued)

OTHER PUBLICATIONS

Leukemia & Lymphoma Society, "NHL Subtypes", downloaded on Oct. 1, 2020 from https://web.archive.org/web/20150509021710/http://www.lls.org/lymphoma/non-hodgkin-lymphoma/diagnosis/nhl-subtypes; web archive capture date May 9, 2015, 2 pages.*
Stamatopoulos et al. (2009) "Antileukemic activity of valproic acid in chronic lymphocytic leukemia B cells defined by microarray analysis," Leukemia, 23(12): 2281-2289.
Tong et al. (2010) "Genome wide DNA methylation profiling of chronic lymphocytic leukemia allows identification of epigenetically repressed molecular pathways with clinical impact," Epigenetics 5(6): 499-508.
Van Damme et al. (2012) "HDAC isoenzyme expression is deregulated in chronic lymphocytic leukemia B-cells and has a complex prognostic significance," Epigen, 7(12): 1403-1412.

(Continued)

*Primary Examiner* — Raymond J Henley, III
(74) *Attorney, Agent, or Firm* — Brian C. Trinque; Lathrop GPM LLP

(57) ABSTRACT

Disclosed are histone deacetylase (HDAC) inhibitors, or combinations comprising an HDAC inhibitor and a Bruton's tyrosine kinase (BTK) inhibitor, for the treatment of chronic lymphocytic leukemia in a subject in need thereof. Also provided herein are methods for treating chronic lymphocytic leukemia in a subject in need thereof comprising administering to the subject a therapeutically effective amount of an HDAC inhibitor, or a combination comprising an HDAC inhibitor and a BTK inhibitor. Other related methods are disclosed.

8 Claims, 15 Drawing Sheets

(56) References Cited

U.S. PATENT DOCUMENTS

| | | |
|---|---|---|
| 2010/0330197 A1 | 12/2010 | Higashiguchi et al. |
| 2011/0218154 A1 | 9/2011 | Schreiber et al. |
| 2012/0121502 A1 | 5/2012 | van Duzer et al. |
| 2012/0190693 A1 | 7/2012 | van Duzer et al. |
| 2013/0225543 A1 | 8/2013 | Jones et al. |
| 2014/0011767 A1 | 1/2014 | Yang et al. |
| 2014/0142104 A1 | 5/2014 | van Duzer et al. |
| 2014/0142117 A1 | 5/2014 | van Duzer et al. |
| 2014/0243345 A1 | 8/2014 | van Duzer et al. |
| 2014/0249148 A1 | 9/2014 | van Duzer et al. |
| 2014/0357512 A1 | 12/2014 | Yang et al. |
| 2015/0045380 A1 | 2/2015 | van Duzer et al. |
| 2015/0099744 A1 | 4/2015 | Tamang et al. |
| 2015/0105358 A1 | 4/2015 | Quayle et al. |
| 2015/0105383 A1 | 4/2015 | Quayle et al. |
| 2015/0105384 A1 | 4/2015 | Jones et al. |
| 2015/0105409 A1 | 4/2015 | Quayle et al. |
| 2015/0150871 A1 | 6/2015 | Quayle et al. |
| 2015/0283142 A1 | 10/2015 | Stern et al. |

FOREIGN PATENT DOCUMENTS

| | | |
|---|---|---|
| WO | 2001/070675 A2 | 9/2001 |
| WO | 2002/074298 A1 | 9/2002 |
| WO | 2003/037869 A1 | 5/2003 |
| WO | 2003/076401 A1 | 9/2003 |
| WO | 2003/076430 A1 | 9/2003 |
| WO | 2004/052869 A1 | 6/2004 |
| WO | 2005/012261 A1 | 2/2005 |
| WO | 2005/028447 A1 | 3/2005 |
| WO | 2005/030705 A1 | 4/2005 |
| WO | 2006/102557 A2 | 9/2006 |
| WO | 2006/123121 A1 | 11/2006 |
| WO | 2007/022638 A1 | 3/2007 |
| WO | 2007/091703 A2 | 8/2007 |
| WO | 2007/130429 A2 | 11/2007 |
| WO | 2007/144341 A1 | 12/2007 |
| WO | 2008/003801 A1 | 1/2008 |
| WO | 2008/033746 A2 | 3/2008 |
| WO | 2008/055068 A2 | 5/2008 |
| WO | 2008/091349 A1 | 7/2008 |
| WO | 2009/137462 A1 | 11/2009 |
| WO | 2009/137503 A1 | 11/2009 |
| WO | 2010/009155 A2 | 1/2010 |
| WO | 2010/011296 A2 | 1/2010 |
| WO | 2010/080996 A1 | 7/2010 |
| WO | 2010/131922 A2 | 11/2010 |
| WO | 2011/011186 A1 | 1/2011 |
| WO | 2011/019393 A2 | 2/2011 |
| WO | 2011/084991 A2 | 7/2011 |
| WO | 2011/146855 A1 | 11/2011 |
| WO | 2011/153514 A2 | 12/2011 |
| WO | 2013/013113 A2 | 1/2013 |
| WO | 2013/059738 A2 | 4/2013 |
| WO | WO 2015/054197 A1 | 4/2015 |
| WO | WO 2016/007423 A1 | 1/2016 |
| WO | WO 2017/184774 A1 | 10/2017 |

OTHER PUBLICATIONS

Mishima et al. (2015) "Mutational Profile and Prognostic Relevance of Circulating Tumor Cells in Multiple Myeloma," Blood, 126 (23).
Bhalla et al. (2009) "PCI-24781 induces caspase and reactive oxygen species-dependent apoptosis through NF-kappaB mechanisms and is synergistic with bortezomib in lymphoma cells," Clin. Cancer Res. 15(10):3354-3365.
Lemal et al. (2011) "Les inhibiteurs des histone-désacétylases en onco-hématologie," Bulletin Du Cancer. 98(8):867-878.—English Abstract Only.
Amengual et al. (2015) "Mechanisms of Acquired Drug Resistance to the Isoform Selective HDAC6 Inhibitor Ricolinostat Reveals Markedly Upregulated Elements of the BTK Pathway Revealing Rational Drug : Drug Combinations," ASH Annual Meeting, Session 605, Abstract 3708.
Scotto et al. (2015) "The ATM Inhibitor KU60019 Synergizes the Antineoplastic Effect of Romidepsin in Mantle Cell Lymphoma (MCL)," Ash Annual Meeting, Session 605, Abstract 3703.
O'Connor et al. (2015) "Targeting Epigenetic Operations with HDAC Inhibitor and Hypomethylating Drugs in Combination Exhibit Synergy in Preclinical and Clinical Experiences in Drug Resistant T-Cell Lymphoma (TCL): A Translational Focus on Doublet Development," ASH Annual Meeting, Session 605, Abstract 1282.
Amengual et al. (2015) "Translational Focus on Targeting HDAC6 with Ricolinostat Confirms Potent Activity in Preclinical Models of Lymphoma and a Favorable Toxicity Profile in Patients with Relapsed or Refractory Lymphoma," ASH Annual Meeting, Molecular Pharmacology, Session 605, Abstract 1280.
Sawas et al. (2015) "The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience," ASH Annual Meeting, Lymphoma: Therapy with Biologic Agents, Session 624, Abstract 586.
Broxterman et al. (1992) "Synthesis of (optically active) sulfur-containing trifunctional amino acids by radical addition to (optically active) unsaturated amino acids," The Journal of Organic Chemistry. 57(23):6286-6294.
Carey et al. (2006) "Histone deacetylase inhibitors: gathering pace," Current Opinion in Pharmacology. 6:369-375.
Chuang et al. (2009) "Multiple roles of HDAC inhibition in neurodegenerative conditions," Trends in Neurosciences. 32(11):591-601.
Dallavalle et al. (2012) "Development and therapeutic impact of HDAC6-selective inhibitors," Biochemical Pharmacology. 84:756-765.
Elaut et al. (2007) "The Pharmaceutical Potential of Histone Deacetylase Inhibitors," Current Pharmaceutical Design. 13:2584-2620.
Foks et al. (1972) "Investigations on Pyrazine Derivatives Part II. Synthesis and Tuberculostatic Action of Some 6Alkylaminopyrazine-2-carboxylic acids," Dissertationes Pharmaceuticae and Pharmacologicae. 24:(6)577-583.
Foks et al. (1974) "Studies on Pyrazine Derivatives," Pol. J. Pharmacol. Pharm. 26:537-543.
Neidle, Stephen: Ed. (2008) Cancer Drug Design and Discovery. Elsevier/Academic Press. pp. 427-431.
Pellicciari et al. (1996) "Synthesis and Pharmacological Characterization of All Sixteen Stereoisomers of 2-(2'-Carboxy-3'-phenylcyclopropyl)glycine. Focus on (2S, 1'S,2'S,3'R)-2-(2'-Carboxy-3'-phenylcyclopropyl)glycine, a Novel and Selective Group II Metabotropic Glutamate Receptors Antagonist," Journal of Medicinal Chemistry. 39(11):2259-2269.
Rajak et al. (2011) "2,5-Disubstituted-1,3,4-oxadiazoles/thiadiazole as Surface Recognition Moiety: Design and Synthesis of Novel Hydroxamic acid Based Histone Deacetylase Inhibitors," Bioorganic & Medicinal Chemistry Letters. 21(19):5735-5738.
Walbrick et al.(1968) "A general method for synthesizing optically active 1,3-disubstituted allene hydrocarbons," The Journal of the American Chemical Society. 90(11):2895-2901.
Warner et al. (1992) "Electron demand in the transition state of the cyclopropylidene to allene ring opening," The Journal of Organic Chemistry. 57(23):6294-6300.
International Preliminary Report on Patentability corresponding to International Patent Application No. PCT/US2011/060791, dated Jul. 22, 2014.
International Search Report with Written Opinion corresponding to International Patent Application No. PCT/US2011/060791, dated Mar. 5, 2014.
Supplementary European Search Report corresponding to European Application No. 11840803.8, dated Mar. 5, 2014.
Santo et al. (2012) "Preclinical activity, pharmacodynamic, and pharmacokinetic properties of a selective HDAC6 inhibitor, ACY-1215, in combination with bortezomib in multiple myeloma," Blood 119(11):2579-2589.

(56) References Cited

OTHER PUBLICATIONS

Sahakian et al. (2011) "The Opposing Role of Histone Deacetylase 10 (HDAC10) and HDAC11 in Proliferation/Survival of Mantle Cell Lymphoma (MCL) and Chronic Lymphocytic Leukemia (CLL)," Blood. vol. 118. No. 21. Abstract No. 1363.

Blum et al. (2009) "Phase II study of the histone deacetylase inhibitor MGCD0103 in patients with previously treated chronic lymphocytic leukaemia," Br. J. Haematol. 147(4): 507-14.

Chou et al. (1984) "Quantitative Analysis of Dose-Effect Relationships: The Combined Effects of Multiple Drugs or Enzyme Inhibitors," Adv. Enzyme Regul. 22: 27-55.

Chou (2010) "Drug Combination Studies and Their Synergy Quantification Using the Chou-Talalay Method," Cancer Research, 70(2): 440-6.

D'Cruz et al. (2013) "Novel Bruton's tyrosine kinase inhibitors currently in development," OncoTargets and Therapy, 6:161-176.

Emanuele et al. (2008) "Histone deacetylase inhibitors: Apoptotic effects and clinical implications (Review)," Int. J. Oncol., 33(4): 637-646.

Holford et al. (1981) "Understanding the Dose-Effect Relationship: Clinical Application of Pharmacokinetic-Pharmacodynamic Models," Clin. Pharmacokinetics 6:429-453.

Wang et al. (2012) "Inhibition of Histone Deacetylase 6 (HDAC6) Disrupts the Tolerogenic STAT3 Signaling Pathway and Augments Antitumor Immune Responses in Mantle Cell Lymphoma (MCL)," Blood. vol. 120. Abstract No. 3724.

Marks (2010) "The clinical development of histone deacetylase inhibitors as targeted anticancer drugs," Expert Opin Investig Drugs, 19(9): 1049-1066.

Raje et al. (Dec. 8, 2011) "Rocilinostat (ACY-1215), a Selective HDAC6 Inhibitor, Alone and in Combination with Bortezomib in Multiple Myeloma: Preliminary Results From the First-in-Humans Phase I/II Study," In; The 54th ASH Annual Meeting and Exposition. Paper No. 4061. Retreived Online at https://ash.confex.com/ash/2012/webprogram/Paper52013.html.—Abstract Only.

Sahakian et al. (2012) "Combination of ACY1215, a Selective Histone Deacetylase 6 (HDAC6) Inhibitor with the Bruton Tyrosine Kinase (BTK) Inhibitor, Ibrutinib, Represents a Novel Therapeutic Strategy in Mantle Cell Lymphoma (MCL)," Blood. 120:1660.

International Search Report with Written Opinion corresponding to International Patent Application No. PCT/US2014/059422, dated Jan. 22, 2015.

Butler et al. (2000) "Suberoylanilide Hydroxamic Acid, an Inhibitor of Histone Deactetylase, Suppresses the Growth of Prostate Cancer Cells in Vitro and in Vivo," Cancer Research. 60:5165-5170.

Costello et al. (Dec. 2012) "Evidence for Changes in RREB-1, ZIP3, and Zinc in the Early Development of Pancreatic Adenocarcinoma," J. Gastrointest. Canc. 43:570-578.

Dokmanovic et al. (2007) "Histone Deacetylase Inhibitors: Overview and Perspectives," Mol. Cancer Res. 5(10):981-989.

Giannini et al. (Jul. 2012) "Histone Deacetylase Inhibitors in the Treatment of Cancer: Overview and Perspectives," Future Med. Chem. 4(11):1439-1460.

Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.

Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.

Lane et al. (2009) "Histone Deacetylase Inhibitors in Cancer Therapy," J. Clin. Oncol. 27:5459-5468.

Loudni et al. (2007) "Design, synthesis and biological evaluation of 1,4-benzodiazepine-2,5-dione-based HDAC inhibitors," Bioorganic and Medicinal Chemistry Letters. 17:4819-4823.

Mazitschek et al. (2008) "Development of a Fluorescence Polarization Based Assay for Histone Deacetylase Ligand Discovery," Bioorganic and Medicinal Chemistry Letters. 18(9):2809-2812.

Miller et al. (1998) "Paclitaxel as the Initial Treatment of Multiple Myeloma: An Eastern Cooperative Oncology Group Study (E1A93)," Am. J. Clin. Oncol. 21(6):553-556.

Perez (1998) "Paclitaxel in Breast Cancer," The Oncologist. 3:373-389.

Ropero et al. (2007) "The Role of Histone Deacetylases (HDACs) in Human Cancer," Molecular Oncology. 1:19-25.

Smil et al. (2009) "Novel HDAC6 Isoform Selective Chiral Small Molecule Histone Deacetylase Inhibitors," Bioorganic and Medicinal Chemistry Letters. 19:688-692.

Spom et al. (2000) "Chemoprevention of Cancer," Carcinogenesis. 21(3):525-530.

Thoppil et al. (Sep. 2011) "Terpenoids as Potential Chemopreventive and Therapeutic Agents in Liver Cancer," World J. Hepatol. 3(9):228-249.

International Search Report with Written Opinion corresponding to International Patent Application No. PCT/US2011/021982, dated Oct. 10, 2011.

Search Opinion corresponding to European Patent Application No. 11735212, dated Jun. 26, 2014.

Written Opinion corresponding to Singapore Patent Application No. Application No. 201205393-0, dated Nov. 15, 2013.

Angibaud et al. (2005) "Discovery of Pyrimidyl-5-hydroxamic acids as New Potent Histone Deacetylase Inhibitors," European Journal of Medicinal Chemistry. 40(6):597-606.

Brana et al. (2002) "Synthesis and biological evaluation of novel 2-(1H-imidazol-4-yl)cyclopropane carboxylic acids: key intermediates for H3 histamine receptor ligands," BioOrganic & Medicinal Chemistry Letter. 12(24):3561-3563.

Chavez et al. (2013) "Ibrutinib: an evidence-based review of its potential in the treatment of advanced chronic lymphocytic leukemia," Core Evidence, 8: 37-45.

Akinleye et al., "Ibrutinib and novel BTK inhibitors in clinical development", *Journal of Hematology & Oncology* 6:59 (2013).

Bottoni et al., "Targeting BTK through microRNA in chronic lymphocytic leukemia", *Blood* 128(26):3101-3112 (2016).

European Examination Report for EP 177865847, dated Apr. 29, 2021, 7 pages.

\* cited by examiner

E.

F.

G.

A.

B.

HDAC INHIBITORS, ALONE OR IN COMBINATION WITH BTK INHIBITORS, FOR TREATING CHRONIC LYMPHOCYTIC LEUKEMIA

RELATED APPLICATIONS

This application is a 35 U.S.C. § 371 filing of International Application No. PCT/US17/28435, filed on Apr. 19, 2017, which claims the benefit of U.S. Provisional Application 62/324,733, filed Apr. 19, 2016. The contents of this application are incorporated herein by reference in its entirety.

TECHNICAL FIELD

The present disclosure relates to methods of treating chronic lymphocytic leukemia with HDAC inhibitors alone or in combination with BTK inhibitors.

BACKGROUND

Currently, major advances have been made to understand the role of histone deactylases (HDACs) in cell proliferation and survival (Emanuele S, et al., Int J Oncol 2008; 33(4): 637-46; Dokmanovic M, et al., Mol Cancer Res 2007; 5(10): 981-9; Marks P A., Expert Opin Investig Drugs 2010; 19(9): 1049-66); however their role in B cell receptor (BCR) signaling in chronic lymphocytic leukemia (CLL) remains unknown. In CLL, an immunosuppressive phenotype enables the malignant B cells to evade immune detection leading to immune suppression. A continuous effort to find targetable molecular mechanisms regulating the expression of such pathways responsible for activation of alternative BCR signaling in CLL may enable achievement of complete response using combinatorial therapies with the goal to stop therapy after. Recently, substantial effort has been given to systematically understand factors that may be involved in transcriptional and post-translational regulation in these processes. In this context, epigenetic modifications have captured special attention. Although epigenetic aberrations involving hyper/hypomethylation of DNA in CLL have been well documented (Tong W G, et al., Epigenetics 2010; 5(6): 499-508), there are very few studies investigating the role histone acetyltransferases HATs and HDACs play in the pathogenesis of this malignancy. In fact, valproic acid (VPA-pan-HDAC inhibitor) (Stamatopoulos B, et al., Leukemia 2009; 23(12): 2281-9) and MGCD0103 (class I) (Blum K A, et al., Br J Haematol 2009; 147(4): 507-14) induced antileukemic activity in CLL, however undesirable side-effects due to non-selectivity remains to be a significant concern.

Additionally, contrary to the well-recognized effects of HDAC inhibitors in the control of cell cycle and apoptosis, HDACs role in BCR signaling pathways is still under investigation. This acknowledged disparity can be attributed, at least in part, to (1) the pan-inhibitory effect of HDAC inhibitors targeting all 11 zinc-dependent HDACs, and (2) the intrinsic differences in the expression profile of these enzymes between different cell types in both physiological and pathological conditions. Therefore, a desirable focus is on investigating iso-selective HDAC inhibitors. Since aberrant over-expression of HDAC6 in CLL cell lines and patient's samples have already been demonstrated (Sahakian E, Blood 2012; 120(21); Van Damme M, et al., Epigen. 2012; 7(12): 1403-12), the mechanistic role of this HDAC in CLL is under investigation.

Ricolinostat is a well-tolerated HDAC6 inhibitor which is now in clinical trials alone or in combination therapy for relapsed- and refractory myeloma (Raje N, et al., ASH Annual Meeting Abstracts. 2012; 120:4061; Vogl D, et al., Blood, Dec. 3, 2015 126 (23)) as well as relapsed-refractory lymphoma (Amengual J E, et al, Poster ASH Annual Meeting 2015). Also, the clinical application and FDA approval of small molecule inhibitor ibrutinib, an inhibitor of Bruton's tyrosine kinase (BTK), has shown remarkable outcome in patients with CLL (Chavez J C, et al., Core evidence 2013; 8: 37-45). BTK inhibition is accompanied by a blockade in proliferation and an increase in apoptosis. However, most patients only reach partial responses with ibrutinib, and some of them still relapse, requiring additional therapies.

Thus, there remains a need in the art to effectively and more permanently treat CLL.

SUMMARY OF THE INVENTION

Provided herein are methods and combinations for treating chronic lymphocytic leukemia (CLL) using HDAC inhibitors alone and in combination with Bruton's tyrosine kinase (BTK) inhibitors. Also provided herein are various methods for achieving specific cellular responses in subjects who have CLL, such as decreasing CLL cell viability, altering expression of inhibitory checkpoint molecules in a T- and/or B-cell compartment, reducing CLL cell expression of IL-10, and decreasing CLL cell proliferation.

In a first aspect, disclosed herein is a method for treating chronic lymphocytic leukemia in a subject in need thereof comprising administering to the subject a therapeutically effective amount of a histone deacetylase 6 (HDAC6) selective inhibitor. In an embodiment, the HDAC6 selective inhibitor is a compound of Formula I:

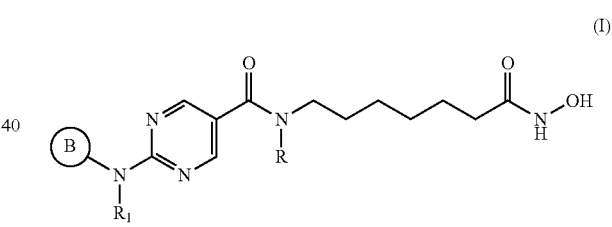

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl.

In another embodiment, the compound of Formula I is compound A:

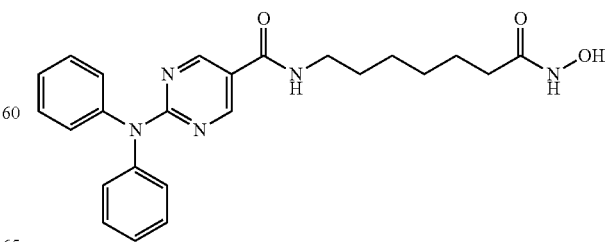

or a pharmaceutically acceptable salt thereof.

In another embodiment, the compound of Formula I is compound B:

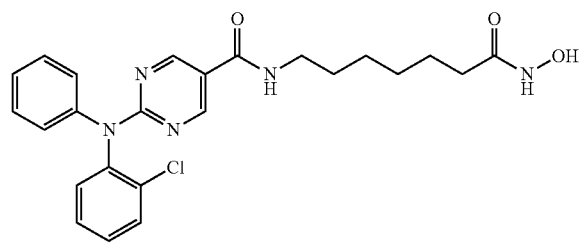 [SMILES: O=C(CCCCCCNC(=O)c1cnc(N(c2ccccc2)c2ccccc2Cl)nc1)NO]

or a pharmaceutically acceptable salt thereof.

In yet other embodiments, the HDAC6 selective inhibitor is a compound of Formula II:

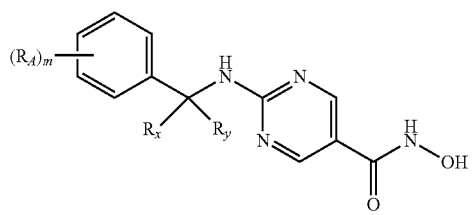

(II)

or a pharmaceutically acceptable salt thereof,
wherein,
$R_x$ and $R_y$ together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2.

In some embodiments, the compound of Formula II is compound C:

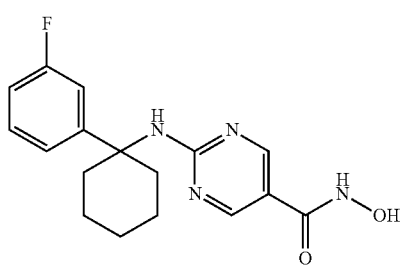 [SMILES: O=C(NO)c1cnc(NC2(c3cccc(F)c3)CCCCC2)nc1]

or a pharmaceutically acceptable salt thereof.

In other embodiments, the compound of Formula II is compound D:

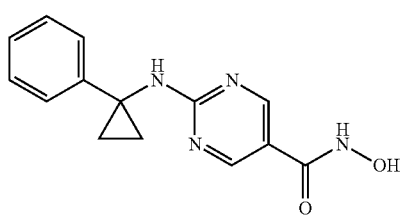 [SMILES: O=C(NO)c1cnc(NC2(c3ccccc3)CC2)nc1]

or a pharmaceutically acceptable salt thereof.

In some embodiments of this first aspect, the method further comprises administering to the subject a therapeutically effective amount of a Bruton's tyrosine kinase (BTK) inhibitor, such as ibrutinib, or a pharmaceutically acceptable salt thereof. In some of these embodiments, the HDAC6 selective inhibitor can be administered at a sub-therapeutic dose.

In some embodiments of this first aspect, the HDAC6 selective inhibitor induces apoptosis of chronic lymphocytic leukemia cells.

In a second aspect, disclosed herein is a pharmaceutical combination for treating chronic lymphocytic leukemia comprising a therapeutically effective amount of a histone deacetylase 6 (HDAC6) selective inhibitor or a pharmaceutically acceptable salt thereof, and a Bruton's tyrosine kinase (BTK) inhibitor or a pharmaceutically acceptable salt thereof. In some embodiments of the pharmaceutical combination, the HDAC6 selective inhibitor is a compound of Formula I:

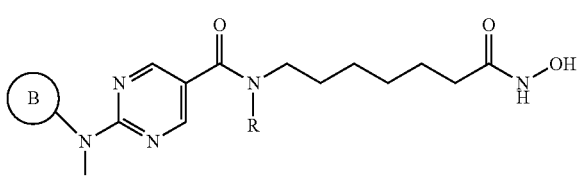

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl.

In another embodiment of the pharmaceutical combination, the compound of Formula I is compound A:

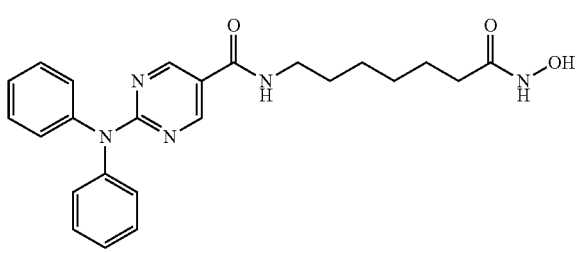 [SMILES: O=C(CCCCCCNC(=O)c1cnc(N(c2ccccc2)c2ccccc2)nc1)NO]

or a pharmaceutically acceptable salt thereof.

In another embodiment of the pharmaceutical combination, the compound of Formula I is compound B:

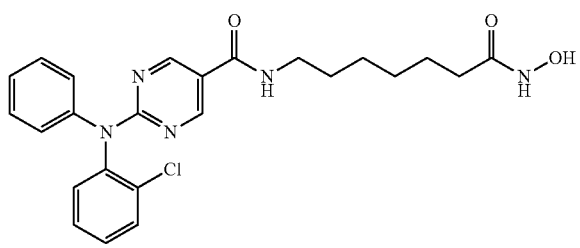 [SMILES: O=C(CCCCCCNC(=O)c1cnc(N(c2ccccc2)c2ccccc2Cl)nc1)NO]

or a pharmaceutically acceptable salt thereof.

In yet other embodiments of the pharmaceutical combination, the HDAC6 selective inhibitor is a compound of Formula II:

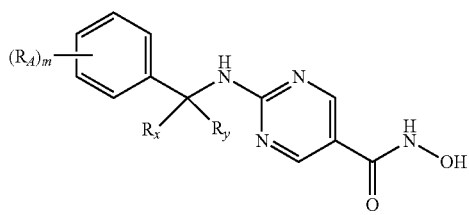

(II)

or a pharmaceutically acceptable salt thereof,
wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2.

In some embodiments of the pharmaceutical combination, the compound of Formula II is compound C:

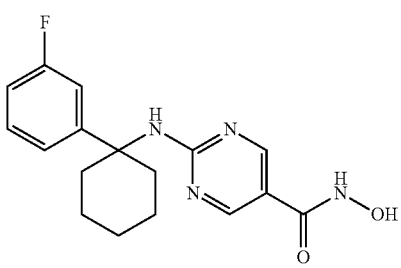 [SMILES: O=C(NO)c1cnc(NC2(c3cccc(F)c3)CCCCC2)nc1]

or a pharmaceutically acceptable salt thereof.

In other embodiments of the pharmaceutical combination, the compound of Formula II is compound D:

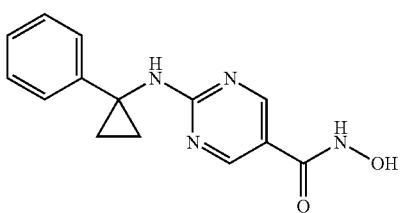 [SMILES: O=C(NO)c1cnc(NC2(c3ccccc3)CC2)nc1]

or a pharmaceutically acceptable salt thereof.

In some embodiments of the pharmaceutical combination, the BTK inhibitor is ibrutinib or a pharmaceutically acceptable salt thereof. The combination can further comprise a pharmaceutically acceptable carrier.

In an embodiment, the pharmaceutical combination comprises Compound A:

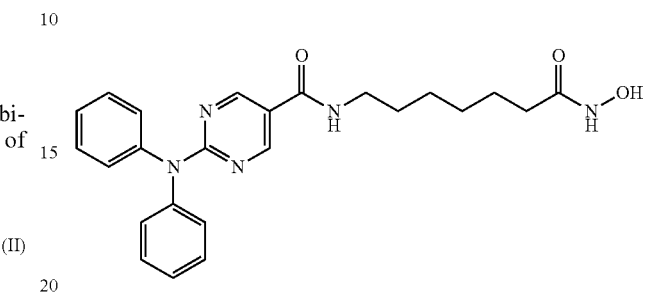

or a pharmaceutically acceptable salt thereof, and ibrutinib, or a pharmaceutically acceptable salt thereof.

In an embodiment, the pharmaceutical combination comprises Compound B:

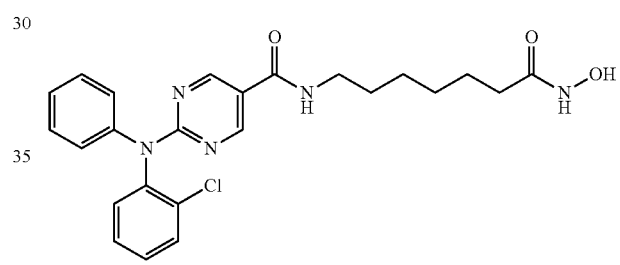

or a pharmaceutically acceptable salt thereof, and ibrutinib, or a pharmaceutically acceptable salt thereof. In an embodiment, the pharmaceutical combination comprises Compound D:

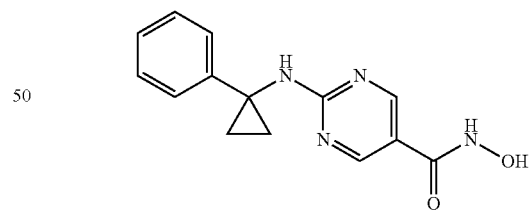

or a pharmaceutically acceptable salt thereof, and ibrutinib, or a pharmaceutically acceptable salt thereof.

In another aspect, disclosed herein is a pharmaceutical composition for treating chronic lymphocytic leukemia in a subject in need thereof comprising a therapeutically effective amount of a histone deacetylase 6 (HDAC6) selective inhibitor or a pharmaceutically acceptable salt thereof, and a Bruton's tyrosine kinase (BTK) inhibitor or a pharmaceutically acceptable salt thereof. In some embodiments of the pharmaceutical composition, the HDAC6 selective inhibitor is a compound of Formula I:

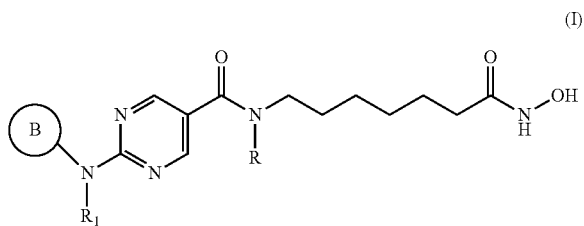

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl.

In another embodiment of the pharmaceutical composition, the compound of Formula I is Compound A:

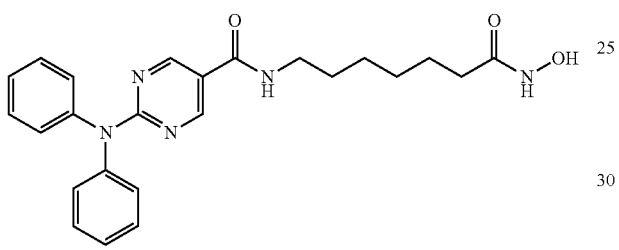

or a pharmaceutically acceptable salt thereof.

In another embodiment of the pharmaceutical composition, the compound of Formula I is Compound B:

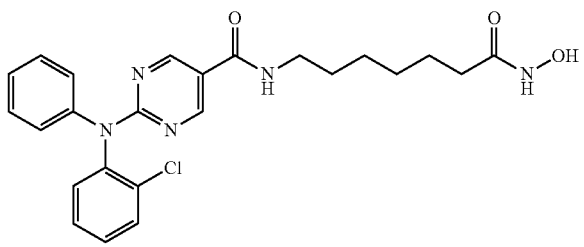 [SMILES: O=C(CCCCCCNC(=O)c1cnc(N(c2ccccc2)c2ccccc2Cl)nc1)NO]

or a pharmaceutically acceptable salt thereof.

In yet other embodiments of the pharmaceutical composition, the HDAC6 selective inhibitor is a compound of Formula II:

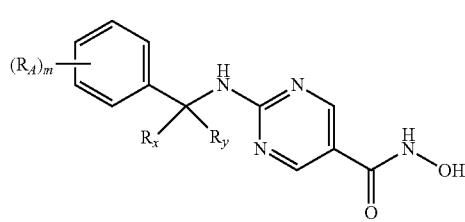

(II)

or a pharmaceutically acceptable salt thereof, wherein,
$R_x$ and $R_y$ together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2.

In some embodiments of the pharmaceutical composition, the compound of Formula II is Compound C:

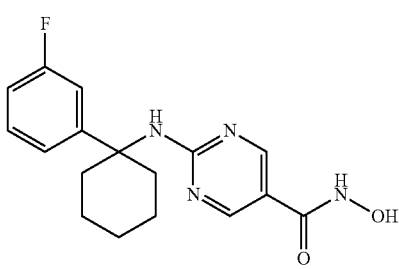 [SMILES: O=C(NO)c1cnc(NC2(c3cccc(F)c3)CCCCC2)nc1]

or a pharmaceutically acceptable salt thereof.

In other embodiments of the pharmaceutical composition, the compound of Formula II is Compound D:

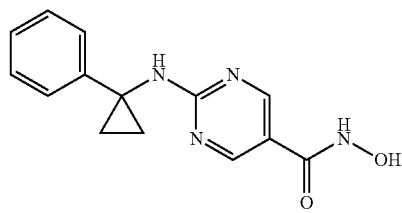 [SMILES: O=C(NO)c1cnc(NC2(c3ccccc3)CC2)nc1]

or a pharmaceutically acceptable salt thereof.

In some embodiments of the pharmaceutical composition, the BTK inhibitor is ibrutinib or a pharmaceutically acceptable salt thereof. The composition can further comprise a pharmaceutically acceptable carrier.

In an embodiment the pharmaceutical composition comprises Compound A:

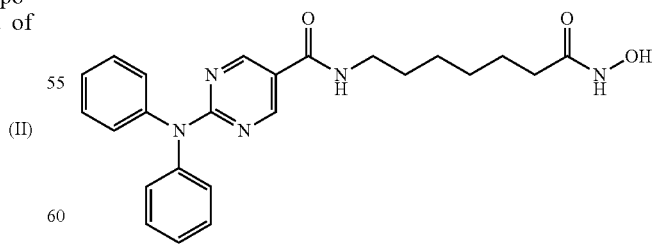

or a pharmaceutically acceptable salt thereof, and ibrutinib, or a pharmaceutically acceptable salt thereof.

In an embodiment the pharmaceutical composition comprises Compound B:

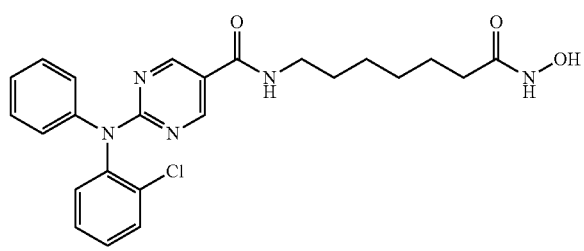 [SMILES: O=C(CCCCCCNC(=O)c1cnc(N(c2ccccc2)c2ccccc2Cl)nc1)NO]

or a pharmaceutically acceptable salt thereof, and ibrutinib, or a pharmaceutically acceptable salt thereof.

In an embodiment the pharmaceutical composition comprises Compound D:

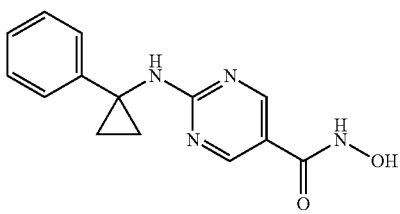 [SMILES: O=C(NO)c1cnc(NC2(c3ccccc3)CC2)nc1]

or a pharmaceutically acceptable salt thereof, and ibrutinib, or a pharmaceutically acceptable salt thereof.

In a third aspect, disclosed herein is a method for decreasing cell viability of chronic lymphocytic leukemia cells in a subject with chronic lymphocytic leukemia in need thereof by administering a histone deacetylase (HDAC) inhibitor, or a combination comprising a HDAC inhibitor and a Bruton's tyrosine kinase (BTK) inhibitor, to the subject.

In a fourth aspect, disclosed herein is a method for synergistically increasing apoptosis of chronic lymphocytic leukemia cells in a subject with chronic lymphocytic leukemia in need thereof by administering a combination comprising a histone deacetylase (HDAC) inhibitor and a Bruton's tyrosine kinase (BTK) inhibitor.

In a fifth aspect, provided herein is a method for altering expression of an inhibitory checkpoint molecule in a T- and/or B-cell compartment in a subject with chronic lymphocytic leukemia in need thereof by administering to the subject a therapeutically effective amount of a histone deacetylase (HDAC) inhibitor, or a combination comprising a HDAC inhibitor and a Bruton's tyrosine kinase (BTK) inhibitor. In some embodiments, the inhibitory checkpoint molecule is selected from the group consisting of: CD274 (PDL-1), CD273 (PDL-2), CD80(B7-1), CD86 (B7-2), CD152 (CTLA4), CD275 (B7RP1), CD276 (B7-H3), B7-H4 (VTCN1), CD270 (HVEM), BLTA, GAL9, CD366 (TIM3), A2aR, CD279 (PD-1), KIR, and CD223 (LAG3), and wherein the expression is reduced. In further embodiments, CD274 (PDL-1) and CD273 (PDL-2) are reduced. In such embodiments, the checkpoint molecule is reduced on effector T lymphocytes (CD4+ or CD8+).

In a sixth aspect, provided herein is a method for altering expression of antigen presenting complexes in a subject with chronic lymphocytic leukemia in need thereof by administering to the subject a therapeutically effective amount of a histone deacetylase (HDAC) inhibitor, or a combination comprising a HDAC inhibitor and a Bruton's tyrosine kinase (BTK) inhibitor. In an embodiment, the presenting protein is MHC I or MHC II, and wherein the expression is increased. In further embodiments, MHC II expression is increased.

In a seventh aspect, provided herein is a method for reducing circulating regulatory T lymphocytes (Tregs) in a subject with chronic lymphocytic leukemia in need thereof by administering to the subject a therapeutically effective amount of a histone deacetylase (HDAC) inhibitor, or a combination comprising a HDAC inhibitor and a Bruton's tyrosine kinase (BTK) inhibitor.

In an eighth aspect, provided herein is a method for reducing IL-10 expression in chronic lymphocytic leukemia cells in a subject with chronic lymphocytic leukemia in need thereof by administering to the subject a therapeutically effective amount of a histone deacetylase (HDAC) inhibitor, or a combination comprising a HDAC inhibitor and a Bruton's tyrosine kinase (BTK) inhibitor.

In a ninth aspect, disclosed herein is a method for decreasing cell proliferation of chronic lymphocytic leukemia cells in a subject with chronic lymphocytic leukemia in need thereof by administering to the subject a therapeutically effective amount of a histone deacetylase (HDAC) inhibitor, or a combination comprising a HDAC inhibitor and a Bruton's tyrosine kinase (BTK) inhibitor.

In yet a tenth aspect, disclosed herein is a method for reducing circulating lymphocytes in a subject with chronic lymphocytic leukemia (CLL) in need thereof, by administering to the subject a therapeutically effective amount of a histone deacetylase (HDAC) inhibitor, or a combination comprising a HDAC inhibitor and a Bruton's tyrosine kinase (BTK) inhibitor.

In an eleventh aspect, disclosed herein is a method for treating chronic lymphocytic leukemia (CLL) in a subject in need thereof, wherein the subject was previously ineffectively treated for CLL with a histone deacetylase 6 (HDAC6) selective inhibitor, the method comprising administering to the subject a therapeutically effective amount of a HDAC6 selective inhibitor and a therapeutically effective amount of a Bruton's tyrosine kinase (BTK) inhibitor.

In a twelfth aspect, disclosed herein is a method for treating chronic lymphocytic leukemia (CLL) in a subject in need thereof, wherein the subject was previously ineffectively treated for CLL with a Bruton's tyrosine kinase (BTK) inhibitor, the method comprising administering to the subject a therapeutically effective amount of a histone deacetylase 6 (HDAC6) selective inhibitor and a therapeutically effective amount of a BTK inhibitor.

In embodiments of the third through tenth aspects, the HDAC inhibitor is a HDAC6 selective inhibitor. In such embodiments, including embodiments of the eleventh and twelfth aspects, the HDAC6 selective inhibitor is a compound of Formula I:

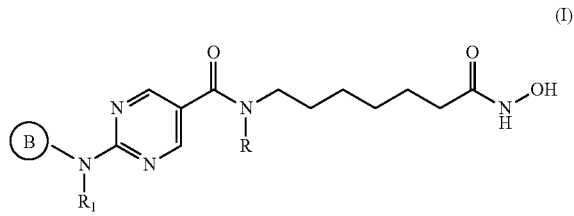

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl.

In another embodiment, the compound of Formula I is Compound A:

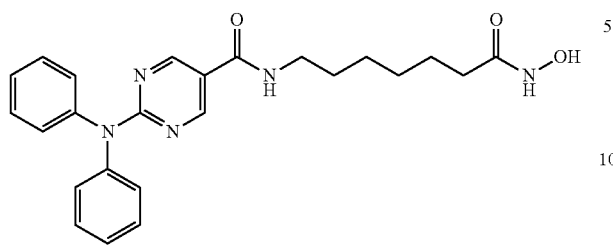

or a pharmaceutically acceptable salt thereof.

In another embodiment, the compound of Formula I is Compound B:

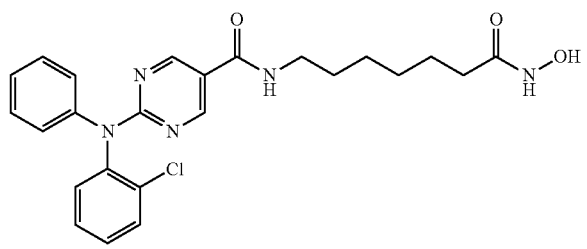 [SMILES: O=C(CCCCCCNC(=O)c1cnc(N(c2ccccc2)c2ccccc2Cl)nc1)NO]

or a pharmaceutically acceptable salt thereof.

In yet other embodiments, the HDAC6 selective inhibitor is a compound of Formula II:

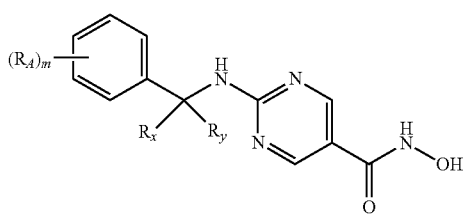

or a pharmaceutically acceptable salt thereof, wherein, $R_x$ and $R_y$ together with the carbon to which each is attached, form a cyclopropyl, cyclobutyl, cyclopentyl, cyclohexyl, cycloheptyl, or cyclooctyl;

each $R_A$ is independently $C_{1-6}$-alkyl, $C_{1-6}$-alkoxy, halo, OH, —$NO_2$, —CN, or —$NH_2$; and m is 0, 1, or 2. In some embodiments, the compound of Formula II is Compound C:

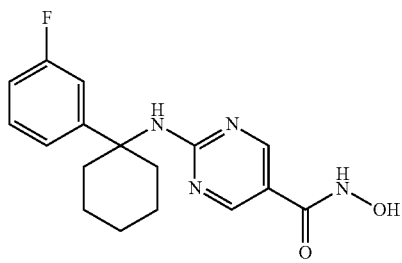 [SMILES: O=C(NO)c1cnc(NC2(c3cccc(F)c3)CCCCC2)nc1]

or a pharmaceutically acceptable salt thereof.

In other embodiments, the compound of Formula II is Compound D:

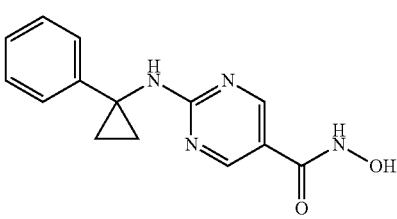 [SMILES: O=C(NO)c1cnc(NC2(c3ccccc3)CC2)nc1]

or a pharmaceutically acceptable salt thereof.

In some embodiments, the method further comprises administering to the subject a therapeutically effective amount of a Bruton's tyrosine kinase (BTK) inhibitor, such as ibrutinib or a pharmaceutically acceptable salt thereof. In some of these embodiments, the HDAC6 selective inhibitor can be administered at a sub-therapeutic dose.

Other objects, features, and advantages will become apparent from the following detailed description. The detailed description and specific examples are given for illustration only because various changes and modifications within the spirit and scope of the invention will become apparent to those skilled in the art from this detailed description. Further, the examples demonstrate the principle of the invention.

BRIEF DESCRIPTION OF THE FIGURES

FIG. 1A shows results of qRT-PCR analysis of HDAC6 expression in twenty B-CLL with Rai stages ranging from 0-4. FIG. 1B shows viability of CLL cell line Mec1 in this experiment as determined using MTS CellTiter 96® (Promega) analysis. Left side of FIG. 1B: Viability compared to non-targeted control counterpart of two polyclonal HDAC6 knock-down (HDAC6KD) cell lines. Right side of FIG. 1B: viability of Mec1 cells transfected with increasing concentrations of HDAC6 over-expressing (H6OE) plasmid, and viability of Mec1 cells treated with two HDAC6 inhibitors at various doses.

FIG. 3C shows Western blot results of PARP and pERK in Mec1 cells treated with Compound A at varying doses (0.5 & 1 μM) alone or in combination with ibrutinib (0.2 & 1 μM) for 24 hrs.

FIG. 4A shows percent survival results from eight mice from eu-TCL1 and euTCL1/HDAC6KO groups that were aged up to 300 days (the day last euTCL1 expired). euTCL1 mice succumb to disease starting day 200 while all eu-TCL1/HDAC6KO mice survived. Spleens from these mice were measured post-mortem and compared. (p value<0.0005***). FIG. 4B shows the disease burden survival advantage of eight C57BL/6 mice adoptively transplanted with 5×10$^6$ splenocytes euTCL1 (or euTCL1-HDAC6KO mice) over euTCL1 splenocyte injected cohort. FIG. 4C shows disease burden in mice treated with Compound D in an aging model of CLL. FIG. 4D shows overall survival (Top) and disease burden (Bottom) of mice receiving Compound D treatment in adoptive transfer experiment model of CLL. FIG. 4E shows overall survival of mice treated with Compound D in an aging model of CLL.

FIG. 5A shows expression of PDL-1 and PDL-2 was reduced and the expression of MHC II was increased in HDAC6KD Mec1 cells when compared to non-target control counterpart. FIG. 5B shows flow cytometry analysis demonstrating normalization of PD-1 and LAG3 on CD4+ T-cells in mice receiving Compound D treatment in the chow (week 10 post adoptive transfer). FIG. 5C shows flow cytometry analysis demonstrating number of T-regs in these mice. FIG. 5D shows the expression of PD-1 and LAG3 molecules on T-regs in mice under the various treatments. FIG. 5E shows a decrease in expression of PD-L1 on the B cells isolated from these treated mice with Compound D when compared to the none-treated animals. Flow cytometry analysis and gating: B-cells (malignant population CD19+/CD5+/CD45R (B220)+/IgM+/Igk+; for normal B-cells CD19+/CD5−/CD45R (B220)+/IgM+/Igk−. T-regs were identified as CD3+/CD4+/CD25 hi/IL-7R low. For co-inhibitory molecule expression CD223 (LAG3), CD279 (PD-1), CD274 (PDL-1), and CD273 (PDL-2). FIG. 5F shows mice adoptively transferred with euTCL1 splenocytes and treated with Compound D (Feed) and Compound A (injection) exhibit lower expression of coinhibitory molecules PD-1 and LAG-3 (10 weeks post adoptive transfer). FIG. 5G shows mice treated with Compound D feed daily in an aging model of CLL exhibit lower PD-1 and LAG-3 expression on T-regs.

FIG. 6A shows mice adoptively transferred with euTCL1 splenocytes and treated with Compound D (Feed) and/or Ibrutinib (Drinking water) as well as combination treatment with both reagents. The data shows a significant decrease in the number of malignant cells in the combinatorial cohort when compared to mice treated with Compound D alone. FIG. 6B shows mice adoptively transferred with euTCL1 splenocytes and treated with Compound D (Feed) and/or Ibrutinib (Drinking water) as well as combination treatment with both reagents.

DETAILED DESCRIPTION

Figure 1:
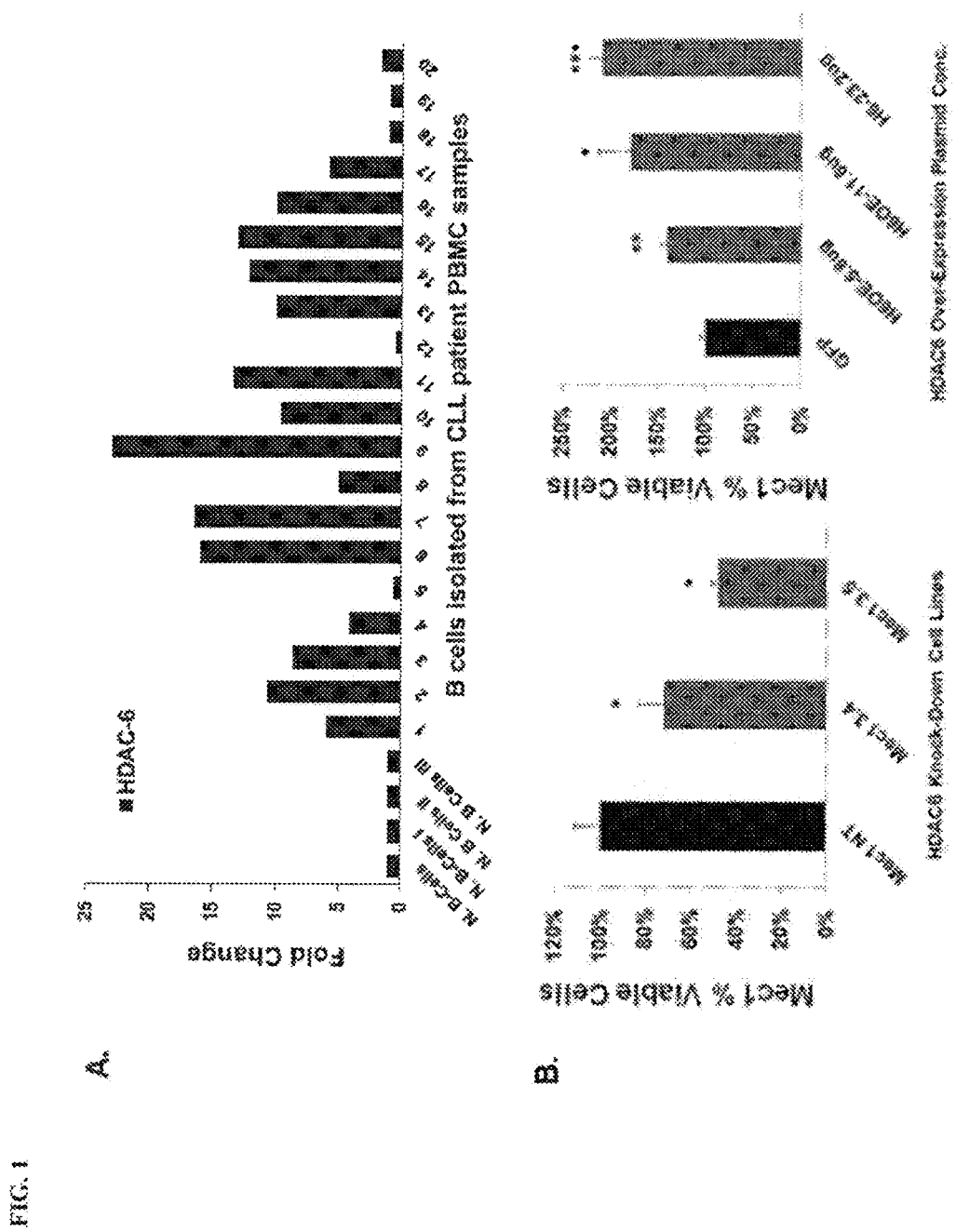
FIGS. 1A-1B show HDAC6 overexpression in human primary B-CLL and altered cell viability in CLL cell lines with modulation of HDAC6 expression.

This disclosure is directed, generally, to HDAC inhibitors, combinations comprising a histone deacetylase (HDAC) inhibitor and a Bruton's tyrosine kinase (BTK) inhibitor, and methods for the treatment of chronic lymphocytic leukemia.

It has been discovered that expression of HDAC6 is increased in CLL patient samples. Furthermore, it has been discovered that selective HDAC6 inhibitors modify the expression of immunomodulatory molecules, which can ultimately lead to increases in the immunogenicity of CLL. It has also been discovered that CLL cells treated with HDAC6 inhibitors show 1) a dose-dependent cell kill, 2) a reduction of IL-10—an important cytokine in the regulation of cell proliferation in CLL, and 3) synergistic reduction of CLL cell viability when combined with the BTK inhibitor ibrutinib. MEC2-HDAC6KD cells exhibit an increase in MHCII and a decrease in PD-L1 expression. It has also been discovered that there is a decrease in the expression of PD-L1 and other immune checkpoint markers in CLL cell lines treated with low-doses of HDAC6 inhibitors. Additionally, malignant B cells isolated from euTCL1 mice and treated ex vivo with HDAC6 inhibitors become more immunogenic and elicit greater type I allogeneic T cell immune response. Lastly, utilizing in vivo CLL murine models (euTCL1 and euTCL1-HDAC6KO), a reduction in circulating lymphocytes is observed in euTCL1-HDAC6KO, as well as euTCL1 mice receiving systemic administration of HDAC6 inhibitors.

Thus, it has been discovered that selective inhibition of HDAC6 in CLL results in the reduction of co-inhibitory molecules, dose dependent increases in cell killing as single treatment, as well as strong synergy when combined with a Bruton's tyrosine kinase (BTK) inhibitor, such as ibrutinib. These combined alterations to the euTCL1 T-cell and B-cell compartments potentially lead to a more favorable immunogenic microenvironment.

Definitions

The definitions below apply to the terms as they are used throughout this specification and claims, unless otherwise limited in specific instances, either individually or as part of a larger group.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "alkoxy" refers to an —O-alkyl moiety.

The terms "cycloalkyl" or "cycloalkylene" denote a monovalent group derived from a monocyclic or polycyclic saturated or partially unsaturated carbocyclic ring compound. Examples of $C_{3-8}$-cycloalkyl include, but are not limited to, cyclopropyl, cyclobutyl, cyclopentyl, cyclohexyl, cycloheptyl and cyclooctyl; and examples of $C_3$-$C_{12}$-cycloalkyl include, but are not limited to, cyclopropyl, cyclobutyl, cyclopentyl, cyclohexyl, bicyclo [2.2.1] heptyl, and bicyclo [2.2.2] octyl. Also contemplated are monovalent groups derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like. In some embodiments, aryl groups have 6 carbon atoms. In some embodiments, aryl groups have from six to ten carbon atoms. In some embodiments, aryl groups have from six to sixteen carbon atoms.

The term "heteroaryl" refers to a mono- or poly-cyclic (e.g., bi-, or tri-cyclic or more) fused or non-fused moiety or ring system having at least one aromatic ring, where one or more of the ring-forming atoms is a heteroatom such as oxygen, sulfur, or nitrogen. In some embodiments, the heteroaryl group has from about one to six carbon atoms, and in further embodiments from one to fifteen carbon atoms. In some embodiments, the heteroaryl group contains five to sixteen ring atoms of which one ring atom is selected from oxygen, sulfur, and nitrogen; zero, one, two, or three ring atoms are additional heteroatoms independently selected from oxygen, sulfur, and nitrogen; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiazolyl, thiadiazolyl, oxadiazolyl, thiophenyl, furanyl, indolyl, quinolinyl, isoquinolinyl, benzimidazolyl, benzooxazolyl, quinoxalinyl, acridinyl, and the like.

The term "halo" refers to a halogen, such as fluorine, chlorine, bromine, and iodine.

The term "combination" refers to two or more therapeutic agents to treat a therapeutic condition or disorder described in the present disclosure. Such combination of therapeutic agents may be in the form of a single pill, capsule, or intravenous solution. However, the term "combination" also encompasses the situation when the two or more therapeutic agents are in separate pills, capsules, or intravenous solutions. Likewise, the term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, or in separate containers (e.g., capsules) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hdal gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6 selective" means that the compound binds to HDAC6 to a substantially greater extent, such as, e.g., 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6 specific. On the other hand, a compound that binds to HDAC6 with an $IC_{50}$ of 50 nM and to HDAC1 with an $IC_{50}$ of 60 nM is not HDAC6 specific The term "inhibitor" is synonymous with the term antagonist.

Histone Deacetylase (HDAC) Inhibitors

Provided herein are compounds and pharmaceutical combinations for the treatment of chronic lymphocytic leukemia in a subject in need thereof. Also provided herein are methods for treating chronic lymphocytic leukemia in a subject in need thereof.

The compounds, combinations, and methods disclosed herein comprise a histone deacetylase (HDAC) inhibitor. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6 selective inhibitor.

In some embodiments, the HDAC6 selective inhibitor is a compound of Formula I:

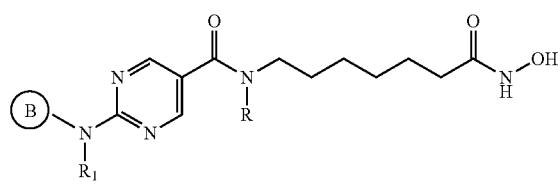

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl.

Representative compounds of Formula I include, but are not limited to Compounds A (ricolinostat) and B, or pharmaceutically acceptable salts thereof.

Compound A

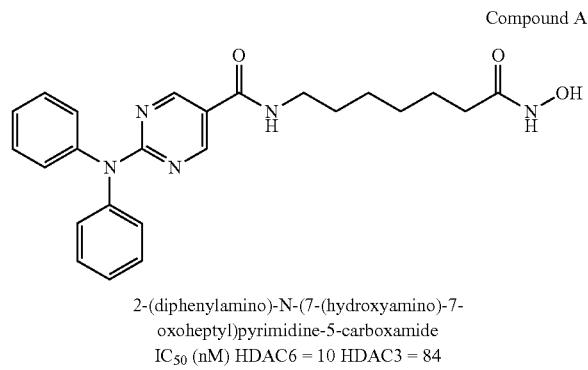

2-(diphenylamino)-N-(7-(hydroxyamino)-7-oxoheptyl)pyrimidine-5-carboxamide
$IC_{50}$ (nM) HDAC6 = 10 HDAC3 = 84

Compound B

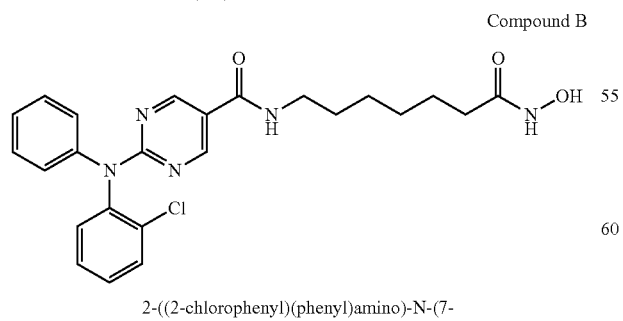

2-((2-chlorophenyl)(phenyl)amino)-N-(7-(hydroxyamino)-7-oxoheptyl)pyrimidine-5-carboxamide
$IC_{50}$ (nM) HDAC6 = 4 HDAC3 = 76

The preparation and properties of selective HDAC6 inhibitors according to Formula I are provided in International Patent Application No. PCT/US2011/021982, the entire contents of which are incorporated herein by reference.

In other embodiments, the HDAC6 selective inhibitor is a compound of Formula II:

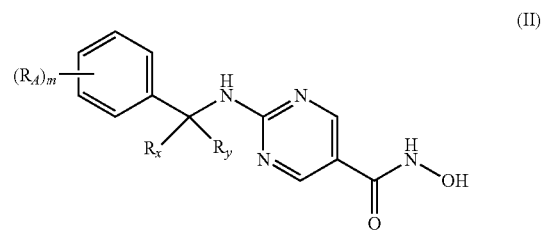

(II)

or a pharmaceutically acceptable salt thereof,
wherein,
$R_x$ and $R_y$, together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2.

Representative compounds of Formula II include, but are not limited to, Compounds C and D, or pharmaceutically acceptable salts thereof.

Compound C

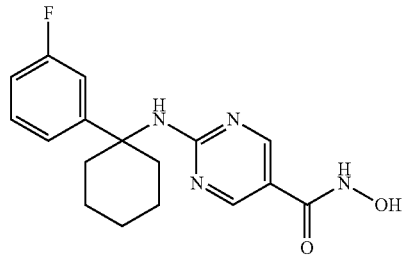

$IC_{50}$ (nM) HDAC6 = 7 HDAC1 = 2123 (283.5x) HDAC2 = 2570 (9343.2x)
HDAC3 = 11223 (1498.8x)

Compound D

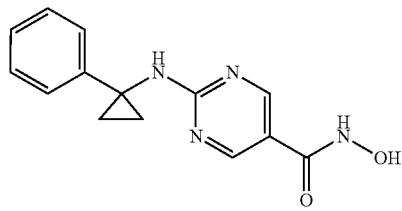

$IC_{50}$ (nM) HDAC6 = 2 HDAC1 = 94 (60x)
HDAC2 = 128 (81.9x) HDAC3 = 219 (139.5x)

The preparation and properties of selective HDAC6 inhibitors according to Formula II are provided in International Patent Application No. PCT/US2011/060791, the entire contents of which are incorporated herein by reference.

In some embodiments, the compounds described herein are unsolvated. In other embodiments, one or more of the compounds are in solvated form. As known in the art, the solvate can be any of pharmaceutically acceptable solvent, such as water, ethanol, and the like.

Although the compounds of Formulas I and II are depicted in their neutral forms, in some embodiments, these compounds are used in a pharmaceutically acceptable salt form. "Pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts of the parent compound formed, for example, from non-toxic inorganic or organic acids. Pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Bruton's Tyrosine Kinase (BTK) Inhibitor

Some embodiments comprise the use of a BTK inhibitor. Some embodiments of the methods also comprise a BTK inhibitor. The BTK inhibitor may be any BTK inhibitor. Preferably, the BTK inhibitor is ibrutinib.

The terms "Bruton's tyrosine kinase inhibitor" and "BTK inhibitor" refer to any compound that reduces a catalytic activity of Bruton's tyrosine kinase (BTK), or homolog thereof, and thereby reduces BTK-mediated signaling.

The term "Bruton's tyrosine kinase (BTK)" refers to Bruton's tyrosine kinase from *Homo sapiens*, as disclosed in, e.g., U.S. Pat. No. 6,326,469 (GenBank Accession No. NP-000052), or a homolog thereof.

The term "Bruton's tyrosine kinase homolog" refers to orthologs of Bruton's tyrosine kinase, e.g., the orthologs from mouse (GenBank Accession No. AAB47246), dog (GenBank Accession No. XP-549139.), rat (GenBank Accession No. NP-001007799), chicken (GenBank Accession No. NP-989564), or zebra fish (GenBank Accession No. XP-698117), and fusion proteins of any of the foregoing that exhibit kinase activity towards one or more substrates of Bruton's tyrosine kinase.

The phrase "BTK-mediated signaling" means any of the biological activities that are dependent on, either directly or indirectly, the activity of BTK. Examples of BTK-mediated signaling are signals that lead to proliferation and survival of BTK-expressing cells, and stimulation of one or more BTK-signaling pathways within BTK-expressing cells.

A BTK "signaling pathway" or "signal transduction pathway" is intended to mean at least one biochemical reaction, or a group of biochemical reactions, that results from the activity of BTK, and which generates a signal that, when transmitted through the signal pathway, leads to activation of one or more downstream molecules in the signaling cascade. Signal transduction pathways involve a number of signal transduction molecules that lead to transmission of a signal from the cell-surface across the plasma membrane of a cell, and through one or more in a series of signal transduction molecules, through the cytoplasm of the cell, and in some instances, into the cell's nucleus. BTK signal transduction pathways ultimately regulate (either enhance or inhibit) the activation of NF-κB via the NF-κB signaling pathway.

In some embodiments, a BTK inhibitor can be an antagonist anti-BTK antibody. In one embodiment, the antagonist anti-BTK antibody is free of significant agonist activity in one cellular response. In another embodiment, the antagonist anti-BTK antibody is free of significant agonist activity in assays of more than one cellular response (e.g., proliferation and differentiation, or proliferation, differentiation, and, for B cells, antibody production).

In other embodiments, the BTK inhibitor can be either a reversible or irreversible small molecule inhibitor (recently reviewed by D'Cruz et al., OncoTargets and Therapy 2013:6 161-176).

The term "irreversible BTK inhibitor" refers to an inhibitor of BTK that can form a covalent bond with an amino acid residue of BTK that results in a reduction of BTK signaling activity. In one embodiment, the irreversible inhibitor of BTK can form a covalent bond with a Cys residue of BTK; in particular embodiments, the irreversible inhibitor can form a covalent bond with a Cys 481 residue (or a homolog thereof) of BTK. Examples of irreversible BTK inhibitors include, but are not limited to, for example, ibrutinib/PCI-32765 (see structure below and U.S. Pat. No. 8,088,781), CNX-774, CC-292, AVL-101, and AVL-291/292.

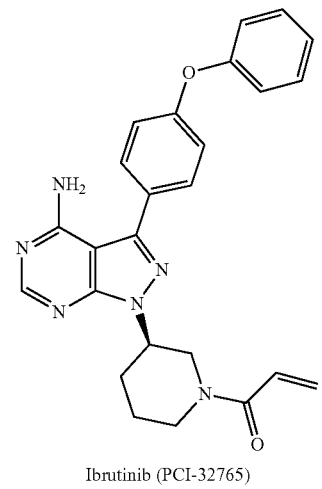 [SMILES: C=CC(=O)N1CCC[C@@H](n2nc(-c3ccc(Oc4ccccc4)cc3)c3c(N)ncnc32)C1]

Ibrutinib (PCI-32765)

The term "reversible BTK inhibitor" refers to an inhibitor of BTK that reversibly binds to BTK to reduce BTK signaling activity. Examples of reversible BTK inhibitors include, but are not limited to Dasatinib (Sprycel/BMS-354825, Bristol-Myers Squibb) [N-(2-chloro-6-methylphenyl)-2-(6-(4-(2-hydroxyethyl) piperazin-1-yl)-2-methylpyrimidin-4-ylamino)thiazole5-carboxamide], LFM-A13, ONO-WG-307, RN-486, and GDC-0834.

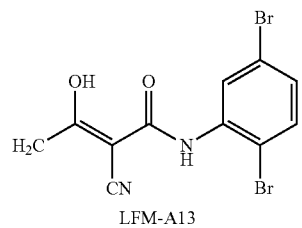

LFM-A13

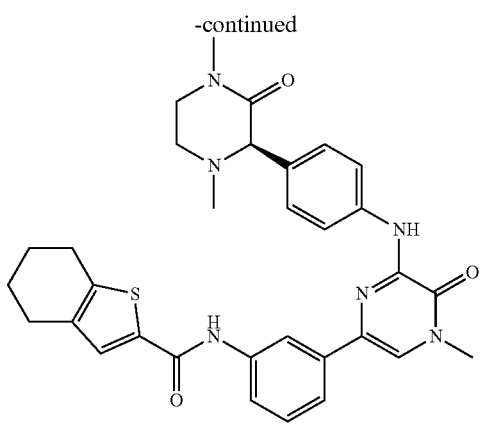

GDC-0834

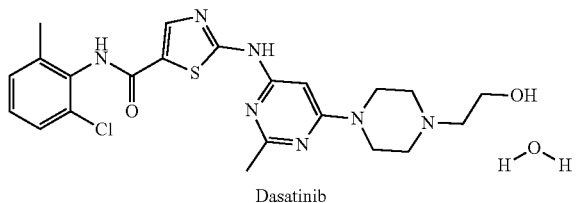

Dasatinib

BTK inhibitors currently in clinical development are reviewed by Akinleye et al. Journal of Hematology & Oncology 2013, 6:59, which is incorporated herein by reference in its entirety.

In some embodiments, the compounds described herein are unsolvated. In other embodiments, one or more of the compounds are in solvated form. As known in the art, the solvate can be any of pharmaceutically acceptable solvent, such as water, ethanol, and the like.

Compositions, Combinations, and Pharmaceutical Compositions and Combinations

Provided herein are compositions and combinations for the treatment of chronic lymphocytic leukemia in a subject in need thereof. Provided in some embodiments are HDAC inhibitors, or combinations comprising a histone deacetylase (HDAC) inhibitor and a Bruton's tyrosine kinase (BTK) inhibitor for the treatment of chronic lymphocytic leukemia in a subject in need thereof. Provided in some embodiments are HDAC inhibitors, or combinations comprising a histone deacetylase (HDAC) inhibitor and a Bruton's tyrosine kinase (BTK) inhibitor for the treatment of chronic lymphocytic leukemia in a subject in need thereof, wherein the combination is administered at dosages that would not be effective when one or both of the compounds are administered alone, but which amounts are effective in combination.

In some embodiments of the compositions and combinations, the HDAC inhibitor is an HDAC6 selective inhibitor. In specific embodiments, the HDAC6 selective inhibitor is a compound of Formula I:

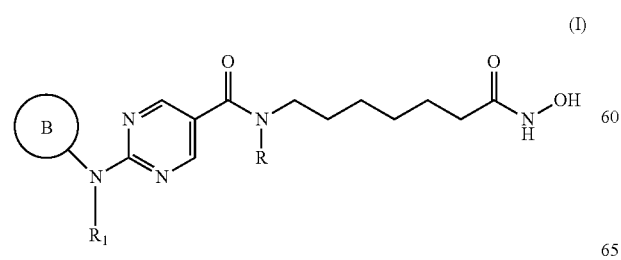

or a pharmaceutically acceptable salt thereof.

In embodiments, the compound of Formula I is Compound A:

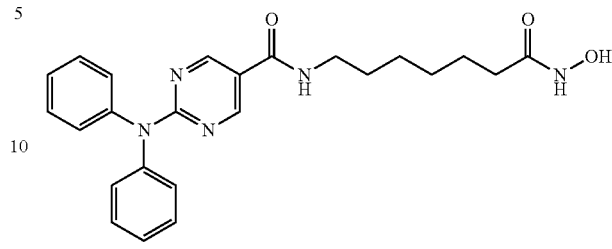

or a pharmaceutically acceptable salt thereof.

In yet other embodiments, the compound of Formula I is Compound B:

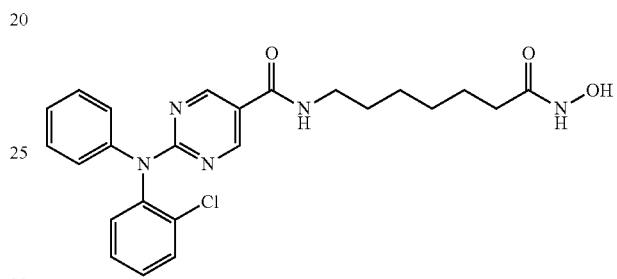

or a pharmaceutically acceptable salt thereof.

In other specific embodiments, the HDAC6 selective inhibitor is a compound of Formula II:

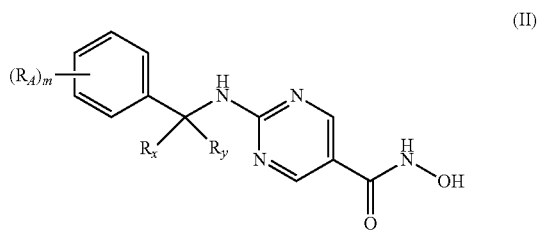

or a pharmaceutically acceptable salt thereof.

In embodiments, the compound of Formula II is Compound C:

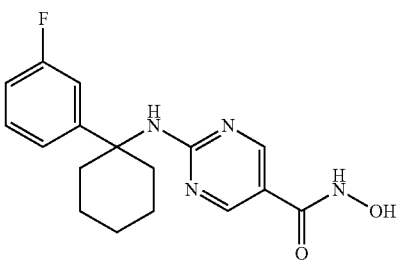 [SMILES: O=C(NO)c1cnc(NC2(c3cccc(F)c3)CCCCC2)nc1]

or a pharmaceutically acceptable salt thereof.

In other embodiments, the compound of Formula II is Compound D:

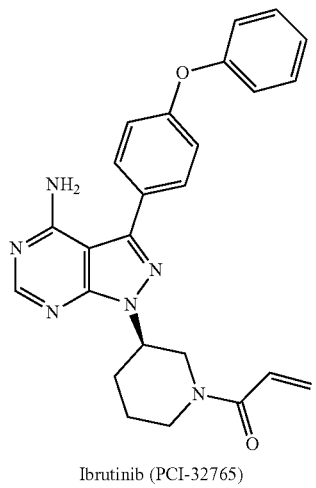

or a pharmaceutically acceptable salt thereof.

In some embodiments of the combinations, the Bruton's tyrosine kinase (BTK) inhibitor is ibrutinib:

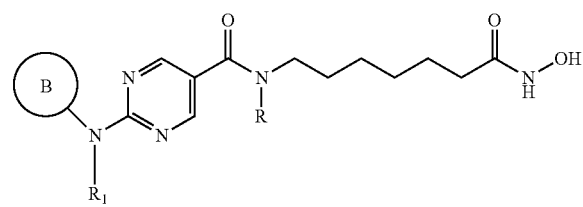

Ibrutinib (PCI-32765)

or a pharmaceutically acceptable salt thereof.

In one embodiment, provided herein is a combination therapy comprising an HDAC6 selective inhibitor and a Bruton's tyrosine kinase (BTK) inhibitor, wherein the HDAC6 selective inhibitor is a compound of Formula I:

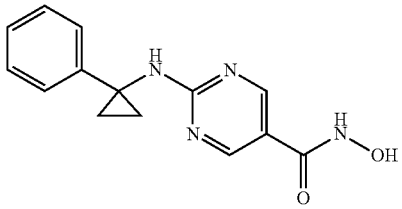 [SMILES: O=C(NO)c1cnc(NC2(c3ccccc3)CC2)nc1]

(I)

or a pharmaceutically acceptable salt thereof,
wherein,
ring B is aryl or heteroaryl;
$R_1$ is an aryl or heteroaryl, each of which may be optionally substituted by OH, halo, or $C_{1-6}$-alkyl; and
R is H or $C_{1-6}$-alkyl; and
the BTK inhibitor is any BTK inhibitor.

In specific embodiments of the combinations the HDAC6 selective inhibitor is:

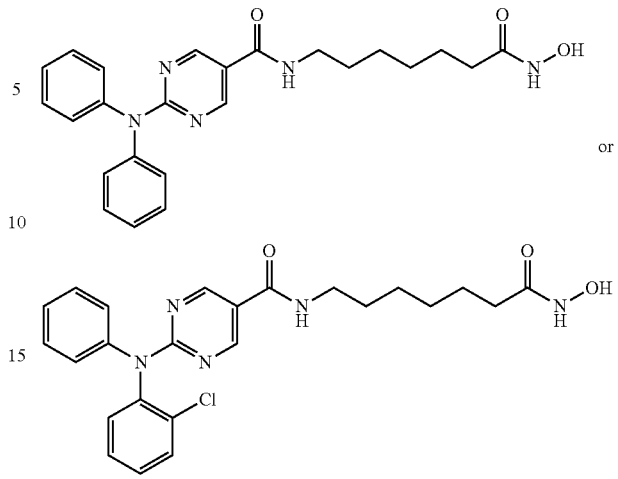

or or pharmaceutically acceptable salts thereof; and
the BTK inhibitor is ibrutinib or a pharmaceutically acceptable salt thereof.

In an embodiment, the combination comprises Compound A:

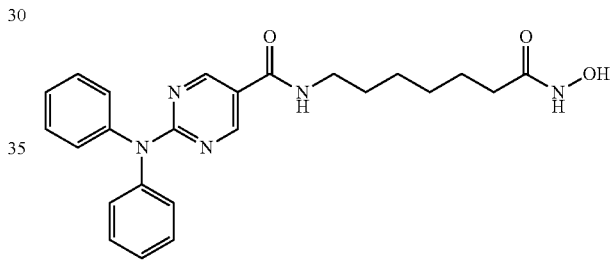

or pharmaceutically acceptable salts thereof; and
the BTK inhibitor is ibrutinib or a pharmaceutically acceptable salt thereof.

In an embodiment, the combination comprises Compound B:

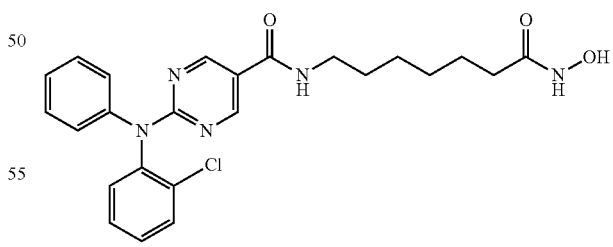

or pharmaceutically acceptable salts thereof; and
the BTK inhibitor is ibrutinib or a pharmaceutically acceptable salt thereof.

In other embodiments, provided herein is a combination therapy comprising an HDAC6 selective inhibitor and a Bruton's tyrosine kinase (BTK) inhibitor, wherein the HDAC6 selective inhibitor is a compound of Formula II:

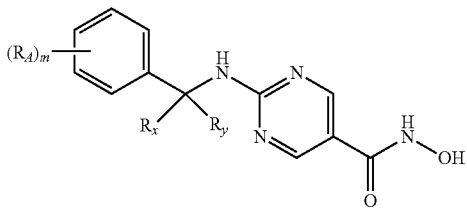

(II)

or a pharmaceutically acceptable salt thereof,
wherein,
$R_x$ and $R_y$ together with the carbon to which each is attached, form a cyclopropyl, cyclobutyl, cyclopentyl, cyclohexyl, cycloheptyl, or cyclooctyl;
each $R_A$ is independently $C_{1-6}$-alkyl, $C_{1-6}$-alkoxy, halo, OH, —$NO_2$, —CN, or —$NH_2$; and
m is 0, 1, or 2; and
the BTK inhibitor any BTK inhibitor.

In specific embodiments of the combinations, the HDAC6 selective inhibitor is:

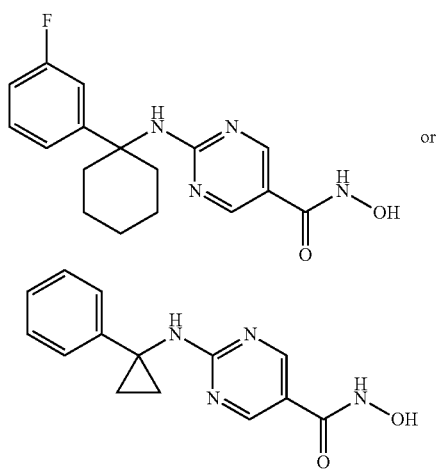

or or a pharmaceutically acceptable salt thereof; and
the BTK inhibitor is ibrutinib or a pharmaceutically acceptable salt thereof.

In an embodiment, the combination comprises Compound D:

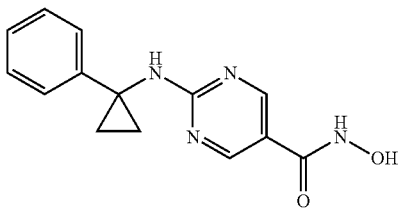 [SMILES: O=C(NO)c1cnc(NC2(c3ccccc3)CC2)nc1]

or pharmaceutically acceptable salts thereof; and
the BTK inhibitor is ibrutinib or a pharmaceutically acceptable salt thereof.

In embodiments, the pharmaceutical combination comprises at least one compound of Formula I and a BTK inhibitor.

In embodiments, the pharmaceutical combination comprises at least one compound of Formula II and a BTK inhibitor.

In embodiments, the pharmaceutical combination comprises at least Compound A and a BTK inhibitor.

In embodiments, the pharmaceutical combination comprises at least Compound B and a BTK inhibitor.

In embodiments, the pharmaceutical combination comprises at least Compound C and a BTK inhibitor.

In embodiments, the pharmaceutical combination comprises at least Compound D and a BTK inhibitor.

In embodiments, the pharmaceutical combination comprises at least one compound of Formula I and ibrutinib.

In embodiments, the pharmaceutical combination comprises at least one compound of Formula II and ibrutinib.

In embodiments, the pharmaceutical combination comprises at least Compound A and ibrutinib.

In embodiments, the pharmaceutical combination comprises at least Compound B and ibrutinib.

In embodiments, the pharmaceutical combination comprises at least Compound C and ibrutinib.

In embodiments, the pharmaceutical combination comprises at least Compound D and ibrutinib.

In embodiments, the pharmaceutical composition comprises at least one compound of Formula I and a BTK inhibitor.

In embodiments, the pharmaceutical composition comprises at least one compound of Formula II and a BTK inhibitor.

In embodiments, the pharmaceutical composition comprises at least Compound A and a BTK inhibitor.

In embodiments, the pharmaceutical composition comprises at least Compound B and a BTK inhibitor.

In embodiments, the pharmaceutical composition comprises at least Compound C and a BTK inhibitor.

In embodiments, the pharmaceutical composition comprises at least Compound D and a BTK inhibitor.

In embodiments, the pharmaceutical composition comprises at least one compound of Formula I and ibrutinib.

In embodiments, the pharmaceutical composition comprises at least one compound of Formula II and ibrutinib.

In embodiments, the pharmaceutical composition comprises at least Compound A and ibrutinib.

In embodiments, the pharmaceutical composition comprises at least Compound B and ibrutinib.

In embodiments, the pharmaceutical composition comprises at least Compound C and ibrutinib.

In embodiments, the pharmaceutical composition comprises at least Compound D and ibrutinib.

Administration/Dose

In some embodiments, the HDAC inhibitor (a compound of Formula I or II) is administered simultaneously with the Bruton's tyrosine kinase (BTK) inhibitor. Simultaneous administration typically means that both compounds enter the patient at precisely the same time. However, simultaneous administration also includes the possibility that the HDAC inhibitor and the Bruton's tyrosine kinase (BTK) inhibitor enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the combination of compounds. In another example, simultaneous administration of separate solutions, one of which contains the HDAC inhibitor and the other of which contains the Bruton's tyrosine kinase (BTK) inhibitor, can be employed. In one example wherein the compounds are in solid form, simultaneous administration can be achieved by administering a composition containing the combination of compounds. Alternatively, simultaneous administration can be achieved by administering two separate compositions, one comprising the HDAC inhibitor and the other comprising the Bruton's tyrosine kinase (BTK) inhibitor.

In other embodiments, the HDAC inhibitor and the Bruton's tyrosine kinase (BTK) inhibitor are not administered simultaneously. In some embodiments, the HDAC inhibitor is administered before the Bruton's tyrosine kinase (BTK) inhibitor. In other embodiments, the Bruton's tyrosine kinase (BTK) inhibitor is administered before the HDAC inhibitor. The time difference in non-simultaneous administrations can be greater than 1 minute, five minutes, 10 minutes, 15 minutes, 30 minutes, 45 minutes, 60 minutes, two hours, three hours, six hours, nine hours, 12 hours, etc. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, one or both of the HDAC inhibitor and the Bruton's tyrosine kinase (BTK) inhibitor are administered in a therapeutically effective amount or dosage. A "therapeutically effective amount" is an amount of HDAC6 selective inhibitor (a compound of Formula I or II) or a Bruton's tyrosine kinase (BTK) inhibitor that, when administered to a patient by itself, effectively treats the chronic lymphocytic leukemia. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the HDAC inhibitor and the Bruton's tyrosine kinase (BTK) inhibitor are administered in a sub-therapeutically effective amount or dosage. A sub-therapeutically effective amount is an amount of HDAC inhibitor (for example, a compound of Formula I or II) or a Bruton's tyrosine kinase (BTK) inhibitor that, when administered to a patient by itself, does not completely inhibit over time the biological activity of the intended target.

Whether administered in therapeutic or sub-therapeutic amounts, the combination of the HDAC inhibitor and the Bruton's tyrosine kinase (BTK) inhibitor should be effective in treating chronic lymphocytic leukemia. For example, a sub-therapeutic amount of the Bruton's tyrosine kinase (BTK) inhibitor can be an effective amount if, when combined with a compound a compound of Formula I or II (HDAC6 selective inhibitor), the combination is effective in the treatment of chronic lymphocytic leukemia.

In some embodiments, the combination of compounds exhibits a synergistic effect (i.e., greater than additive effect) in the treatment of the chronic lymphocytic leukemia. The term "synergistic effect" refers to the action of two agents, such as, for example, a HDAC inhibitor and a Bruton's tyrosine kinase (BTK) inhibitor, producing an effect, for example, slowing the symptomatic progression of cancer or symptoms thereof, which is greater than the simple addition of the effects of each drug administered alone. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. In some embodiments, the combination of compounds exhibits a synergistic effect (i.e., greater than additive effect) in the treatment of chronic lymphocytic leukemia (CLL). Table I describes CI ranges used to determine synergy.

TABLE 1

Recommended Symbols for Describing Synergism or Antagonism in Drug Combination Studies Analyzed with the Combination Index (CI) Method

| Range of CI | Symbol | Description |
|---|---|---|
| <0.1 | +++++ | Very strong synergism |
| 0.1-0.3 | ++++ | Strong synergism |
| 0.3-0.7 | +++ | Synergism |
| 0.7-0.85 | ++ | Moderate synergism |
| 0.85-0.90 | + | Slight synergism |
| 0.90-1.10 | ± | Nearly additive |
| 1.10-1.20 | − | Slight antagonism |
| 1.20-1.45 | −− | Moderate antagonism |
| 1.45-3.30 | −−− | Antagonism |
| 3.3-10 | −−−− | Strong antagonism |
| >10 | −−−−− | Very strong antagonism |

In different embodiments, depending on the combination and the effective amounts used, the combination of compounds can inhibit cancer growth, achieve cancer stasis, or even achieve substantial or complete cancer regression.

While the amounts of a HDAC inhibitor and a Bruton's tyrosine kinase (BTK) inhibitor should result in the effective treatment of the chronic lymphocytic leukemia, the amounts, when combined, are preferably not excessively toxic to the patient (i.e., the amounts are preferably within toxicity limits as established by medical guidelines). In some embodiments, either to prevent excessive toxicity and/or provide a more efficacious treatment of the chronic lymphocytic leukemia, a limitation on the total administered dosage is provided. Typically, the amounts considered herein are per day; however, half-day and two-day or three-day cycles also are considered herein.

Different dosage regimens may be used to treat the chronic lymphocytic leukemia. In some embodiments, a daily dosage, such as any of the exemplary dosages described above, is administered once, twice, three times, or four times a day for three, four, five, six, seven, eight, nine, or ten days. Depending on the stage and severity of the chronic lymphocytic leukemia, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

In some embodiments, each dosage contains both an HDAC inhibitor and a Bruton's tyrosine kinase (BTK) inhibitor to be delivered as a single dosage, while in other embodiments each dosage contains either a HDAC inhibitor and a Bruton's tyrosine kinase (BTK) inhibitor to be delivered as separate dosages.

Compounds of Formula I or II, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC inhibitor and the BTK inhibitor of the pharmaceutical combination can be administered in a single unit dose or separate dosage forms. Accordingly, the phrase "pharmaceutical combination" includes a combination of two drugs in either a single dosage form or a separate dosage forms, i.e., the pharmaceutically acceptable carriers and excipients described throughout the application can be combined with an HDAC inhibitor and a BTK inhibitor in a single unit dose, as well as individually combined with a HDAC inhibitor and a BTK inhibitor when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC inhibitors or Bruton's tyrosine kinase (BTK) inhibitors described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Methods

Disclosed herein are methods for treating chronic lymphocytic leukemia in a subject in need thereof comprising administering to the subject an HDAC inhibitor, or a pharmaceutical combination as disclosed herein. Thus, provided herein are methods for treating chronic lymphocytic leukemia in a subject in need thereof comprising administering to the subject a therapeutically effective amount of an HDAC inhibitor, such as an HDAC6 selective inhibitor, or a combination comprising an HDAC inhibitor, such as a HDAC6 selective inhibitor, and a Bruton's tyrosine kinase (BTK) inhibitor.

The subject is typically a human. However, the subject can be any mammal for which treatment is desired. Thus, the methods described herein can be applied to both human and veterinary applications.

The terms "treating" or "treatment" indicate that the method has, at the least, mitigated abnormal cellular proliferation. For example, the method can reduce the rate of cellular growth in a patient, or prevent the continued growth or spread of chronic lymphocytic leukemia, or even reduce the overall reach of the chronic lymphocytic leukemia. Inhibition of abnormal cell growth can occur by a variety of mechanisms including, but not limited to, cell death, apoptosis, arrest of mitosis, inhibition of cell division, transcription, translation, transduction, etc.

In an embodiment, provided herein is a method for treating chronic lymphocytic leukemia in a subject in need thereof comprising administering to the subject a therapeutically effective amount of a compound of Formula I, or a pharmaceutically acceptable salt thereof.

In another embodiment, provided herein is a method for treating chronic lymphocytic leukemia in a subject in need thereof comprising administering to the subject a therapeutically effective amount of a compound of Formula II, or a pharmaceutically acceptable salt thereof.

In a further embodiment, provided herein is a method for treating chronic lymphocytic leukemia in a subject in need thereof comprising administering to the subject a therapeutically effective amount of Compound A or a pharmaceutically acceptable salt thereof.

In another embodiment, provided herein is a method for treating chronic lymphocytic leukemia in a subject in need thereof comprising administering to the subject a therapeutically effective amount of Compound B or a pharmaceutically acceptable salt thereof.

In another embodiment, provided herein is a method for treating chronic lymphocytic leukemia in a subject in need thereof comprising administering to the subject a therapeutically effective amount of Compound C or a pharmaceutically acceptable salt thereof.

In another embodiment, provided herein is a method for treating chronic lymphocytic leukemia in a subject in need thereof comprising administering to the subject a therapeutically effective amount of Compound D or a pharmaceutically acceptable salt thereof.

In another embodiment, provided herein is a method for treating chronic lymphocytic leukemia in a subject in need thereof comprising administering to the subject a therapeutically effective amount of a compound of Formula I, or a pharmaceutically acceptable salt thereof, and ibrutinib.

In another embodiment, provided herein is a method for treating chronic lymphocytic leukemia in a subject in need thereof comprising administering to the subject a therapeutically effective amount of a compound of Formula II, or a pharmaceutically acceptable salt thereof, and ibrutinib.

In another embodiment, provided herein is a method for treating chronic lymphocytic leukemia in a subject in need thereof comprising administering to the subject a therapeutically effective amount of Compound A and ibrutinib.

In another embodiment, provided herein is a method for treating chronic lymphocytic leukemia in a subject in need thereof comprising administering to the subject a therapeutically effective amount of Compound B and ibrutinib.

In another embodiment, provided herein is a method for treating chronic lymphocytic leukemia in a subject in need thereof comprising administering to the subject a therapeutically effective amount of Compound C and ibrutinib.

In another embodiment, provided herein is a method for treating chronic lymphocytic leukemia in a subject in need thereof comprising administering to the subject a therapeutically effective amount of Compound D and ibrutinib.

In an embodiment, cell viability of chronic lymphocytic leukemia cells are decreased in a subject with chronic lymphocytic leukemia by administering an HDAC inhibitor, or a combination comprising an HDAC inhibitor and a BTK inhibitor, to the subject. Preferably, the HDAC inhibitor is an HDAC6 selective inhibitor. The HDAC6 selective inhibitor can comprise one of the Compounds A-D. Preferably, the BTK inhibitor is ibrutinib.

In an embodiment, apoptosis of chronic lymphocytic leukemia cells is synergistically increased by administering to a subject with chronic lymphocytic leukemia a combination comprising an HDAC inhibitor and a BTK inhibitor. Preferably, the HDAC inhibitor is an HDAC6 selective inhibitor. The HDAC6 selective inhibitor can comprise one of the Compounds A-D. Preferably, the BTK inhibitor is ibrutinib.

In an embodiment, the expression of an inhibitory checkpoint molecule in a T- and/or B-cell compartment in a subject with chronic lymphocytic leukemia is altered by administering to the subject a therapeutically effective amount of a HDAC inhibitor, or a combination comprising a HDAC inhibitor and a BTK inhibitor. In such embodiments, where expression is reduced, these checkpoint molecules are selected from the group consisting of CD274 (PDL-1), CD273 (PDL-2), CD80 (B7-1), CD86 (B7-2), CD152 (CTLA4), CD275 (B7RP1), CD276 (B7-H3), B7-H4 (VTCN1), CD270 (HVEM), BLTA, GAL9, CD366 (TIM3), A2aR, CD279 (PD-1), KIR, and CD223 (LAG3). In some embodiments, these checkpoint molecules are CD274 (PDL-1) and CD273 (PDL-2). The checkpoint molecule is reduced on regulatory T lymphocytes (Tregs) in yet further embodiments. Preferably, the HDAC inhibitor is an HDAC6 selective inhibitor. The HDAC6 selective inhibitor can comprise one of the Compounds A-D. Preferably, the BTK inhibitor is ibrutinib.

In another embodiment, the expression of an antigen presenting complex is altered in a subject with chronic lymphocytic leukemia by administering to the subject a therapeutically effective amount of a HDAC inhibitor, or a combination comprising a HDAC inhibitor and a BTK inhibitor. In such embodiments, the antigen presenting complex molecule is MHC I or MHC II, and expression is increased. In further embodiments, MHC II is increased. Preferably, the HDAC inhibitor is an HDAC6 selective inhibitor. The HDAC6 selective inhibitor can comprise one of the Compounds A-D. Preferably, the BTK inhibitor is ibrutinib.

In another embodiment, circulating regulatory T lymphocytes (Tregs) are reduced in a subject with chronic lymphocytic leukemia by administering to the subject a therapeutically effective amount of a HDAC inhibitor, or a combination comprising a HDAC inhibitor and a BTK inhibitor. Preferably, the HDAC inhibitor is an HDAC6 selective inhibitor. The HDAC6 selective inhibitor can comprise one of the Compounds A-D. Preferably, the BTK inhibitor is ibrutinib.

In another embodiment, IL-10 expression is reduced in chronic lymphocytic leukemia cells in a subject with chronic lymphocytic leukemia by administering to the subject a therapeutically effective amount of a HDAC inhibitor, or a combination comprising a HDAC inhibitor and a BTK inhibitor. Preferably, the HDAC inhibitor is an HDAC6 selective inhibitor. The HDAC6 selective inhibitor can comprise one of the Compounds A-D. Preferably, the BTK inhibitor is ibrutinib.

In another embodiment, cell proliferation is decreased in a subject with chronic lymphocytic leukemia by administering to the subject a therapeutically effective amount of a HDAC inhibitor, or a combination comprising a HDAC inhibitor and a BTK inhibitor. Preferably, the HDAC inhibitor is an HDAC6 selective inhibitor. The HDAC6 selective inhibitor can comprise one of the Compounds A-D. Preferably, the BTK inhibitor is ibrutinib.

In another embodiment, circulating tumor lymphocytes are reduced in a subject with chronic lymphocytic leukemia by administering to the subject a therapeutically effective amount of a HDAC inhibitor, or a combination comprising a HDAC inhibitor and a BTK inhibitor. Preferably, the HDAC inhibitor is an HDAC6 selective inhibitor. The HDAC6 selective inhibitor can comprise one of the Compounds A-D. Preferably, the BTK inhibitor is ibrutinib.

In yet another embodiment, provided herein is a method for treating chronic lymphocytic leukemia in a subject, wherein the subject was previously ineffectively treated for chronic lymphocytic leukemia with a HDAC6 selective inhibitor, the method comprising administering to the subject a therapeutically effective amount of a HDAC6 selective inhibitor and a therapeutically effective amount of a BTK inhibitor. The HDAC6 selective inhibitor can comprise one of the Compounds A-D. The BTK inhibitor can be ibrutinib.

In another embodiment, provided herein is a method for treating chronic lymphocytic leukemia in a subject in need thereof, wherein the subject was previously ineffectively treated for chronic lymphocytic leukemia with a BTK inhibitor, the method comprising administering to the subject a therapeutically effective amount of a HDAC6 selective inhibitor and a therapeutically effective amount of a BTK inhibitor. The HDAC6 selective inhibitor can comprise one of the Compounds A-D. The BTK inhibitor can be ibrutinib.

In another aspect, provided herein is a method of treating CLL in a subject in need thereof comprising administering to the patient a therapeutically effective amount of Formula I or Formula II, or a pharmaceutically acceptable salt thereof, and ibrutinib, or a pharmaceutically acceptable salt thereof. In an embodiment Formula I or Formula II and ibrutinib are administered at dosages and over time intervals that produce a synergistic effect.

In another aspect, provided herein is a method of treating CLL in a subject in need thereof comprising administering to the patient a therapeutically effective amount of Compound A, or a pharmaceutically acceptable salt thereof, and ibrutinib, or a pharmaceutically acceptable salt thereof. In an embodiment Compound A and ibrutinib are administered at dosages and over time intervals that produce a synergistic effect.

In another aspect, provided herein is a method of treating CLL in a subject in need thereof comprising administering to the patient a therapeutically effective amount of Compound B, or a pharmaceutically acceptable salt thereof, and ibrutinib, or a pharmaceutically acceptable salt thereof. In an embodiment Compound B and ibrutinib are administered at dosages and over time intervals that produce a synergistic effect.

In another aspect, provided herein is a method of treating CLL in a subject in need thereof comprising administering to the patient a therapeutically effective amount of Compound C, or a pharmaceutically acceptable salt thereof, and ibrutinib, or a pharmaceutically acceptable salt thereof. In an embodiment Compound C and ibrutinib are administered at dosages and over time intervals that produce a synergistic effect.

In another aspect, provided herein is a method of treating CLL in a subject in need thereof comprising administering to the patient a therapeutically effective amount of Compound D, or a pharmaceutically acceptable salt thereof, and ibrutinib, or a pharmaceutically acceptable salt thereof. In an embodiment Compound D and ibrutinib are administered at dosages and over time intervals that produce a synergistic effect.

In an embodiment, provided herein is a HDAC6 selective inhibitor and a BTK inhibitor for use in therapy.

In an embodiment, provided herein is a compound of Formula I and a BTK inhibitor for use in therapy.

In an embodiment, provided herein is a compound of Formula II and a BTK inhibitor for use in therapy.

In an embodiment, provided herein is a Compound A and a BTK inhibitor for use in therapy.

In an embodiment, provided herein is a Compound B and a BTK inhibitor for use in therapy.

In an embodiment, provided herein is a Compound C and a BTK inhibitor for use in therapy.

In an embodiment, provided herein is a Compound D and a BTK inhibitor for use in therapy.

In an embodiment, provided herein is a compound of Formula I and a BTK inhibitor for use in treating CLL in a subject in need thereof.

In an embodiment, provided herein is a compound of Formula II and a BTK inhibitor for use in treating CLL in a subject in need thereof.

In an embodiment, provided herein is a Compound A and a BTK inhibitor for use in treating CLL in a subject in need thereof.

In an embodiment, provided herein is a Compound B and a BTK inhibitor for use in treating CLL in a subject in need thereof.

In an embodiment, provided herein is a Compound C and a BTK inhibitor for use in treating CLL in a subject in need thereof.

In an embodiment, provided herein is a Compound D and a BTK inhibitor for use in treating CLL in a subject in need thereof. In an embodiment, provided herein is an HDAC6 selective inhibitor for use in treating CLL in a subject in need thereof, wherein the HDAC6 selective inhibitor is for use in combination with a BTK inhibitor.

In an embodiment, provided herein is a compound of Formula I for use in treating CLL in a subject in need thereof, wherein the compound of Formula I is for use in combination with a BTK inhibitor.

In an embodiment, provided herein is a compound of Formula II for use in treating CLL in a subject in need thereof, wherein the compound of Formula I is for use in combination with a BTK inhibitor.

In an embodiment, provided herein is Compound A for use in treating CLL in a subject in need thereof, wherein Compound A is for use in combination with a BTK inhibitor.

In an embodiment, provided herein is Compound B for use in treating CLL in a subject in need thereof, wherein Compound B is for use in combination with a BTK inhibitor.

In an embodiment, provided herein is Compound C for use in treating CLL in a subject in need thereof, wherein Compound C is for use in combination with a BTK inhibitor.

In an embodiment, provided herein is Compound D for use in treating CLL in a subject in need thereof, wherein Compound D is for use in combination with a BTK inhibitor.

In an embodiment, provided herein is an HDAC6 selective inhibitor and a BTK inhibitor for use in combination therapy for treating CLL in a subject in need thereof, wherein the HDAC6 selective inhibitor and the BTK inhibitor are for concurrent, sequential or separate administration.

In an embodiment, provided herein is a compound of Formula I and a BTK inhibitor for use in combination therapy for treating CLL in a subject in need thereof, wherein the compound of formula I and the BTK inhibitor are for concurrent, sequential or separate administration.

In an embodiment, provided herein is a compound of Formula II and a BTK inhibitor for use in combination therapy for treating CLL in a subject in need thereof, wherein the compound of formula II and the BTK inhibitor are for concurrent, sequential or separate administration.

In an embodiment, provided herein is Compound A and a BTK inhibitor for use in combination therapy for treating CLL in a subject in need thereof, wherein Compound A and the BTK inhibitor are for concurrent, sequential or separate administration.

In an embodiment, provided herein is Compound B and a BTK inhibitor for use in combination therapy for treating CLL in a subject in need thereof, wherein Compound B and the BTK inhibitor are for concurrent, sequential or separate administration.

In an embodiment, provided herein is Compound C and a BTK inhibitor for use in combination therapy for treating CLL in a subject in need thereof, wherein Compound C and the BTK inhibitor are for concurrent, sequential or separate administration.

In an embodiment, provided herein is Compound D and a BTK inhibitor for use in combination therapy for treating CLL in a subject in need thereof, wherein Compound D and the BTK inhibitor are for concurrent, sequential or separate administration.

In an embodiment of the pharmaceutical combination, the ratio of HDAC6 selective inhibitor to BTK inhibitor is in the range of 700:1-1:40. In another embodiment, the ratio of HDAC6 selective inhibitor to BTK inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Formula I to BTK inhibitor is in the range of 700:1-1:40. In another embodiment of the pharmaceutical combination, the ratio of Formula I to BTK inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Formula II to BTK inhibitor is in the range of 700:1-1:40. In another embodiment of the pharmaceutical combination, the ratio of Formula II to BTK inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound A to BTK inhibitor is in the range of 700:1-1:40. In another embodiment of the pharmaceutical combination, the ratio of Compound A to BTK inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound B to BTK inhibitor is in the range of 700:1-1:40. In another embodiment of the pharmaceutical combination, the ratio of Compound B to BTK inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound C to BTK inhibitor is in the range of 700:1-1:40. In another embodiment of the pharmaceutical combination, the ratio of Compound C to BTK inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound D to BTK inhibitor is in the range of 700:1-1:40. In another embodiment of the pharmaceutical combination, the ratio of Compound D to BTK inhibitor is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound A to ibrutinib is in the range of 700:1-1:40. In another embodiment of the pharmaceutical combination, the ratio of Compound A to ibrutinib is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound B to ibrutinib is in the range of 700:1-1:40. In another embodiment of the pharmaceutical combination, the ratio of Compound B to ibrutinib is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound C to ibrutinib is in the range of 700:1-1:40. In another embodiment of the pharmaceutical combination, the ratio of Compound C to ibrutinib is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In an embodiment of the pharmaceutical combination, the ratio of Compound D to ibrutinib is in the range of 700:1-1:40. In another embodiment of the pharmaceutical combination, the ratio of Compound D to ibrutinib is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

Kits

In other embodiments, kits are provided. Kits include package(s) comprising compounds or compositions disclosed herein. In some embodiments, kits comprise a HDAC inhibitor or a pharmaceutically acceptable salt thereof, or a HDAC inhibitor or a pharmaceutically acceptable salt thereof and a BTK inhibitor or a pharmaceutically acceptable salt thereof.

"Package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering the disclosed compounds or compositions to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments. However, the scope of the claims is not to be in any way limited by the examples set forth herein. Various changes and modifications to the disclosed embodiments will be apparent to those skilled in the art and such changes and modifications including, without limitation, those relating to the disclosed chemical structures, substituents, derivatives, formulations and/or methods may be made without departing from the spirit of the invention and the scope of the appended claims. Definitions of the variables in the structures in the schemes herein are commensurate with those of corresponding positions in the formulae presented herein.

The synthesis of the compounds of Formula I (e.g., Compounds A and B) is provided in PCT/US2011/021982, which is incorporated herein by reference in its entirety. The synthesis of compounds of Formula II (e.g., Compounds C and D) is provided in PCT/US2011/060791, which is incorporated herein by reference in its entirety.

Example 1: Synthesis of 2-(diphenylamino)-N-(7-(hydroxyamino)-7-oxoheptyl)pyrimidine-5-carboxamide (Compound A)

Reaction Scheme

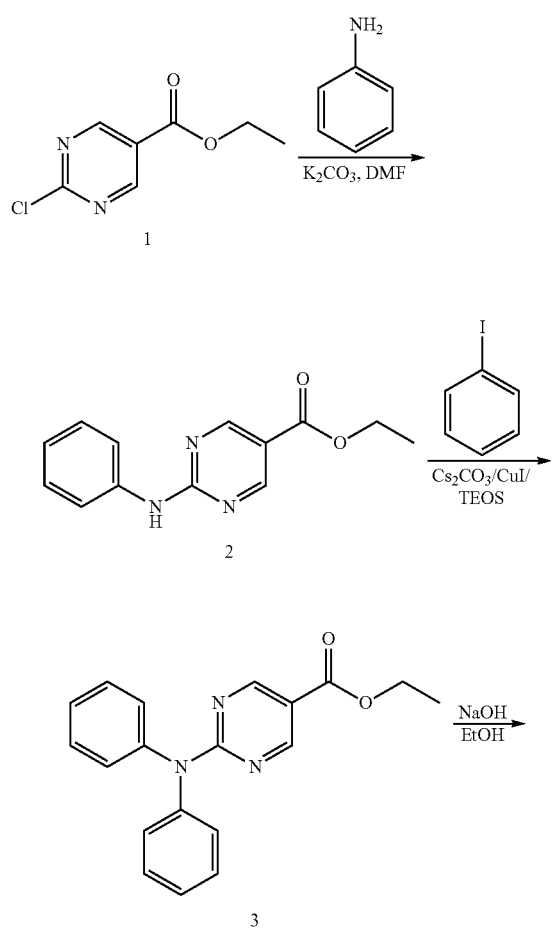

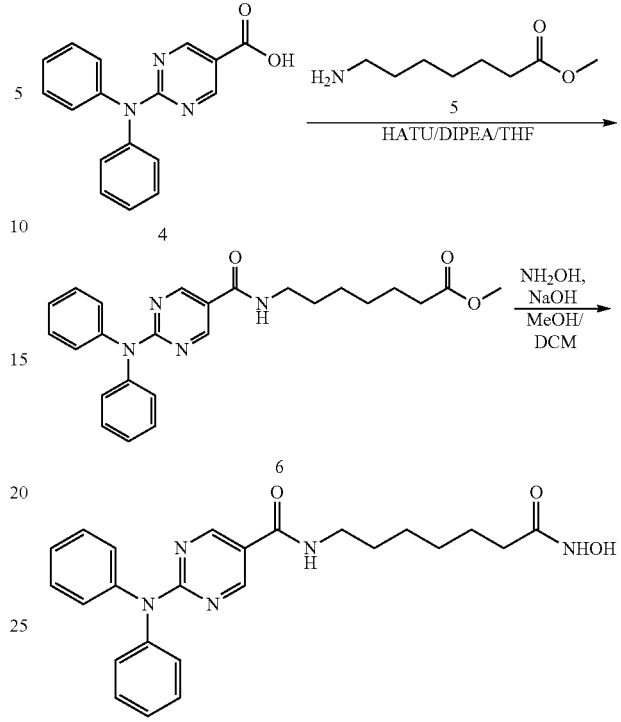

Synthesis of Intermediate 2: A mixture of aniline (3.7 g, 40 mmol), compound 1 (7.5 g, 40 mmol), and $K_2CO_3$ (11 g, 80 mmol) in DMF (100 ml) was degassed and stirred at 120° C. under $N_2$ overnight. The reaction mixture was cooled to r.t. and diluted with EtOAc (200 ml), then washed with saturated brine (200 ml×3). The organic layers were separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3: A mixture of compound 2 (6.2 g, 25 mmol), iodobenzene (6.12 g, 30 mmol), CuI (955 mg, 5.0 mmol), $Cs_2CO_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and $NH_4F$—$H_2O$ on silica gel [50 g, pre-prepared by the addition of $NH_4F$ (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4: 2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over $Na_2SO_4$. Removal of the solvent gave a brown solid (2.5 g, 92%).

Synthesis of Intermediate 6: A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide (Compound A): A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 2: Synthesis of 2-((2-chlorophenyl)(phenyl)amino)-N-(7-(hydroxyamino)-7-oxoheptyl)pyrimidine-5-carboxamide (Compound B)

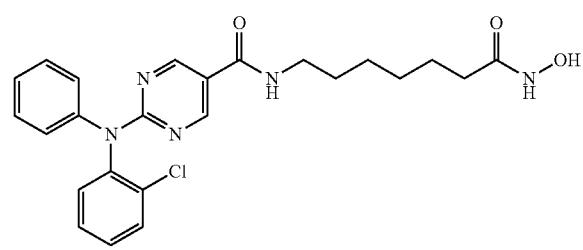 [SMILES: O=C(CCCCCCNC(=O)c1cnc(N(c2ccccc2)c2ccccc2Cl)nc1)NO]

Reaction Scheme:

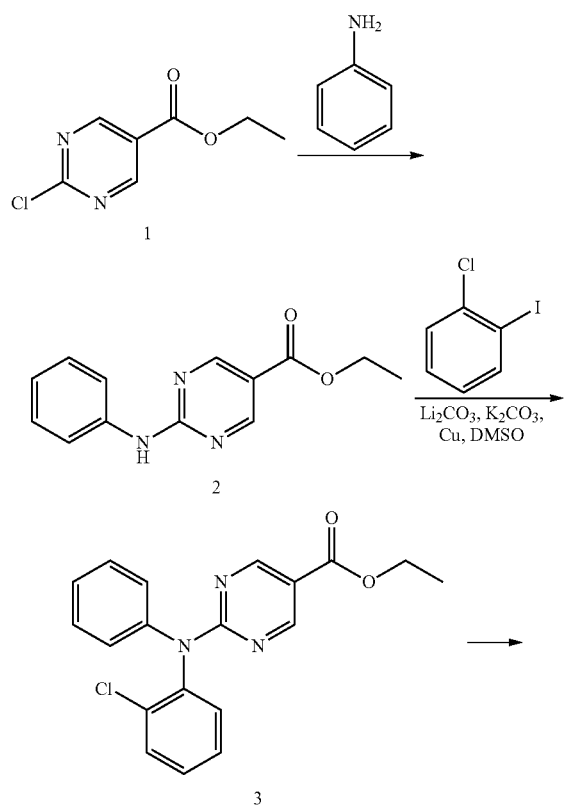

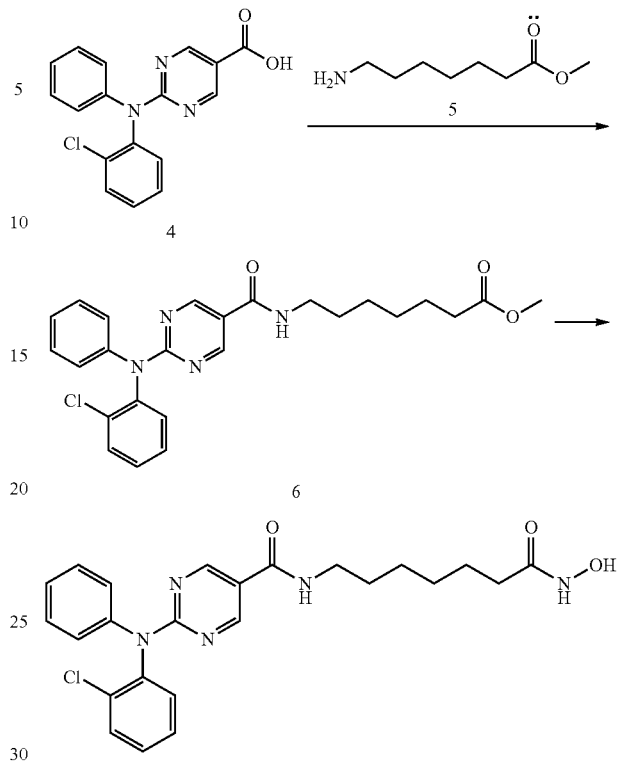

Synthesis of Intermediate 2: See synthesis of intermediate 2 in Example 1.

Synthesis of Intermediate 3: A mixture of compound 2 (69.2 g, 1 equiv.), 1-chloro-2-iodobenzene (135.7 g, 2 equiv.), Li$_2$CO$_3$ (42.04 g, 2 equiv.), K$_2$CO$_3$ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4: See synthesis of intermediate 4 in Example 1.

Synthesis of Intermediate 6: See synthesis of intermediate 6 in Example 1.

Synthesis of 2-((2-chlorophenyl)(phenyl)amino)-N-(7-(hydroxyamino)-7-oxoheptyl)pyrimidine-5-carboxamide (Compound B): See synthesis of Compound A in Example 1.

Example 3: Synthesis of 2-((1-(3-fluorophenyl)cyclohexyl)amino)-N-hydroxypyrimidine-5-carboxamide (Compound C)

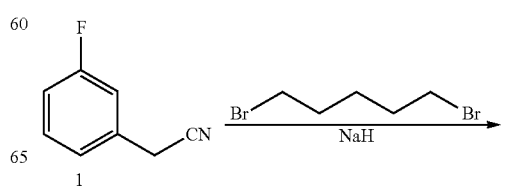

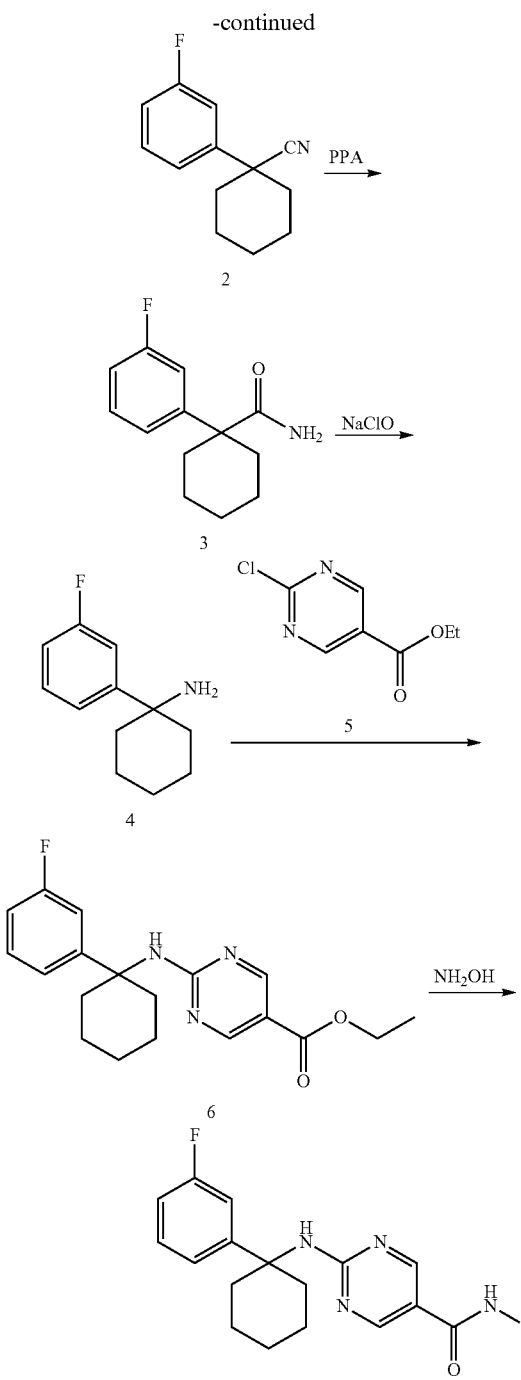

Synthesis of Intermediate 2: To a solution of compound 1 (100 g, 0.74 mol) in dry DMF (1000 ml) was added 1,5-dibromopentane (170 g, 0.74 mol). NaH (65 g, 2.2 eq) was added dropwise while the reaction was cooled in an ice bath. The resulting mixture was vigorously stirred overnight at 50° C. The suspension was carefully quenched with ice water and extracted with ethyl acetate (3×500 ml). The combined organic layers were concentrated to afford the crude product, which was purified by flash column chromatography to give compound 2 as pale solid (100 g, 67%).

Synthesis of Intermediate 3: A solution of compound 2 (100 g, 0.49 mol) in PPA (500 ml) was heated at 110° C. for about 5-6 hours. After completion, the resulting mixture was carefully adjusted to a pH of about 8-9 with sat. NaHCO₃ solution. The resulting precipitate was collected and washed with water (1000 ml) to afford compound 3 as white solid (95 g, 87%).

Synthesis of Intermediate 4: To a solution of compound 3 (95 g, 0.43 mol) in n-BuOH (800 ml) was added NaCl (260 ml, 1.4 eq). 3N NaOH (400 ml, 2.8 equiv.) was then added at 0° C. and the reaction was stirred overnight at r.t. The resulting mixture was extracted with EA (2×500 ml), and the combined organic layers washed with brine. The solvent was removed in vacuo to afford the crude product which was further purified by treatment with HCl salt to yield compound 4 as a white powder (72 g, 73%).

Synthesis of Intermediate 6: To a solution of compound 4 (2.29 g 10 mmol) in dioxane (50 ml) was added compound 5 (1.87 g, 1.0 equiv.) and DIPEA (2.58 g, 2.0 equiv.). The mixture was heated overnight at 110-120° C. The resulting mixture was directly purified on silica gel column to afford the coupled product, compound 6, as a white solid (1.37 g, 40%).

Synthesis of 2-((1-(3-fluorophenyl)cyclohexyl) amino)-N-hydroxypyrimidine-5-carboxamide (Compound C)

To a solution of compound 6 (100 mg, 0.29 mmol) in MeOH/DCM (10 ml, 1:1) was added 50% NH₂OH in water (2 ml, excess). Sat. NaOH in MeOH (2 ml, excess) was then added at 0° C. and the reaction was stirred for 3-4 hours. After completion, the resulting mixture was concentrated and acidified with 2N HCl to reach a pH of 4-5. The precipitate was collected and washed with water (10 ml) to remove excess NH₂OH. Drying the precipitate afforded 2-((1-(3-fluorophenyl)cyclohexyl)amino)-N-hydroxypyrimidine-5-carboxamide as a white powder (70 mg, 73%).

Example 4: Synthesis of N-hydroxy-2-((1-phenylcyclopropyl)amino)pyrimidine-5-carboxamide (Compound D)

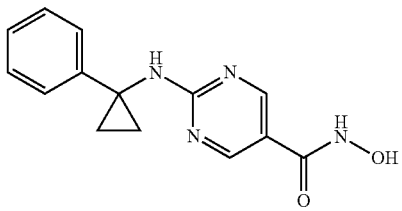 [SMILES: O=C(NO)c1cnc(NC2(c3ccccc3)CC2)nc1]

Reaction Scheme

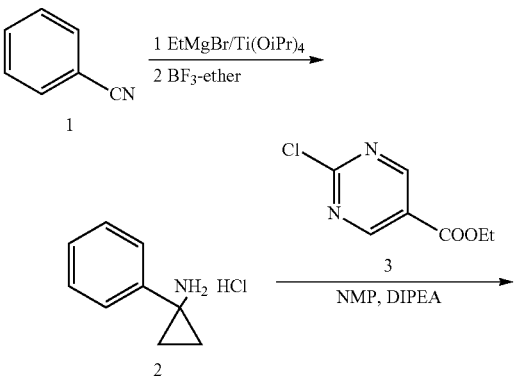

-continued

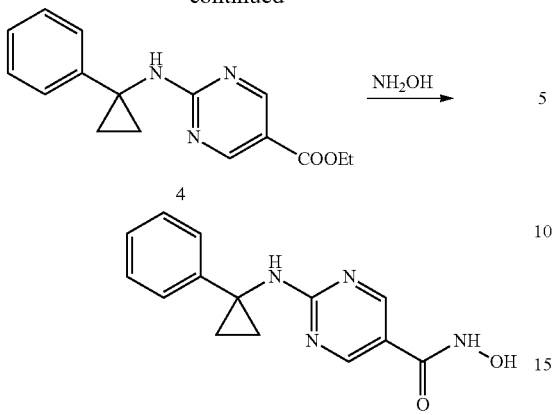

Synthesis of Intermediate 2: A solution of compound 1, benzonitrile, (250 g, 1.0 equiv.), and Ti(OiPr)$_4$ (1330 ml, 1.5 equiv.) in MBTE (3750 ml) was cooled to about −10 to −5° C. under a nitrogen atmosphere. EtMgBr (1610 ml, 3.0M, 2.3 equiv.) was added dropwise over a period of 60 min., during which the inner temperature of the reaction was kept below 5° C. The reaction mixture was allowed to warm to 15-20° C. for 1 hr. BF$_3$-ether (1300 ml, 2.0 equiv.) was added dropwise over a period of 60 min., while the inner temperature was maintained below 15° C. The reaction mixture was stirred at 15-20° C. for 1-2 hr. and stopped when a low level of benzonitrile remained. 1N HCl (2500 ml) was added dropwise while maintaining the inner temperature below 30° C. NaOH (20%, 3000 ml) was added dropwise to bring the pH to about 9.0, while still maintaining a temperature below 30° C. The reaction mixture was extracted with MTBE (3×2) and EtOAc (3×2), and the combined organic layers were dried with anhydrous Na$_2$SO$_4$ and concentrated under reduced pressure (below 45° C.) to yield a red oil. MTBE (2500 ml) was added to the oil to give a clear solution, and upon bubbling with dry HCl gas, a solid precipitated. This solid was filtered and dried in vacuum yielding 143 g of compound 2.

Synthesis of Intermediate 4: Compound 2 (620 g, 1.0 equiv) and DIPEA (1080 g, 2.2 equiv. were dissolved in NMP (3100 ml) and stirred for 20 min. Compound 3 (680 g, 1.02 equiv.) was added and the reaction mixture was heated to about 85-95° C. for 4 hrs. The solution was allowed to slowly cool to r.t. This solution was poured onto H$_2$O (20 L) and much of the solid was precipitated out from the solution with strong stirring. The mixture was filtered and the cake was dried under reduced pressure at 50° C. for 24 hr., yielding 896 g of compound 4 (solid, 86.8%).

Synthesis of N-hydroxy-2-((1-phenylcyclopropyl)amino) pyrimidine-5-carboxamide (Compound D): A solution of MeOH(1000 ml) was cooled to about 0-5° C. with stirring. NH$_2$OH HCl (1107 g, 10 equiv.) was added, followed by careful addition of NaOCH$_3$ (1000 g, 12.0 equiv.) The resulting mixture was stirred at 0-5° C. for one hr., and was filtered to remove the solid. Compound 4 (450 g, 1.0 equiv.) was added to the reaction mixture in one portion, and stirred at 10° C. for two hours until compound 4 was consumed. The reaction mixture was adjusted to a pH of about 8.5-9 through addition of HCl (6N), resulting in precipitation. The mixture was concentrated under reduced pressure. Water (3000 ml) was added to the residue with intense stirring and the precipitate was collected by filtration. The product was dried in an oven at 45° C. overnight (340 g, 79% yield).

Example 5: Other Materials and Methods

Example 5.1: Flow Cytometry Immunophenotyping

Flow cytometric analysis of peripheral blood mononuclear cells (PBMCs) was performed using fluorochrome-labeled monoclonal antibodies and the vitality dye 4',6-diamidino-2-phenylindole. Data was acquired on an LSRII cytometer (Becton, Dickinson and Company; Franklin Lakes, NJ), and analyzed with FlowJo software (FlowJo; Ashland, Oreg). Absolute cell numbers calculated using AccuCheck Counting beads (ThermoFisher Scientific; Waltham, MA).

Example 5.2: qRT-PCR

Total RNA was isolated from all samples using TRIzol® (ThermoFisher Scientific) with manufacturer-supplied protocols. cDNA was generated using iScript™ (BioRad; Hercules, CA) and IQ Syber Green Supermix (Qiagen; Germantown, MD) was utilized in all qRT-PCR reactions.

Example 5.3: SYTOX® Green (ThermoScientific) (CellTox Assay)

From 10,000 to 25,000 cells per well of each cell line were plated and treated with DMSO or HDAC inhibitors for 48 hrs. in conjunction with reagent. Fluorescence was recorded once a day on a Cytation3 Monometer/Luminometer (BioTeck; Winooski, VA) following manufacturer supplied protocols.

Example 5.4: Immunoblotting

Cells were lysed in a lysis buffer, and samples were then resolved on 10% gels and transferred to nitrocellulose membranes. Bands were detected by scanning blots with an LI-COR Odyssey (LI-COR; Lincoln, NE) imaging system.

Example 5.5: HDAC6 Inhibitors

Compound A is an injectable (i.p.) form of HDAC6 inhibitor currently in use for clinical trials in multiple myeloma and lymphoma. Compound D is a selective HDAC6 inhibitor which can be made available in animal feed ("chow") which provides constant but low level exposure.

Example 5.5: Animal Studies

All animal studies involving euTCL1 and its cross with HDAC6KO were performed following established protocols that followed approved Institutional Animal Care and Use Committee (IACUC) procedures. Two mouse models of CLL were used: an Aging CLL model, and an Accelerated CLL Model.
A) Aging CLL Model
  Birth
  euTCL1 (CLL model mouse) and
  euTCL1/HDAC6KO transgenic mice
  5-7 Months
  Flow cytometry analysis
  For analysis of disease
  9 Months
  Flow cytometry analysis
  For analysis of disease 12 Months
Flow cytometry analysis
For analysis of disease
Observe for survival
B) Accelerated CLL Model
Day 0
Adoptive transfer of 5×10$^6$ euTCL1 or euTCL1/1-IDAC6KO splenocytes
Week 3-5
Flow cytometry analysis
For analysis of disease
Week 9
Flow cytometry analysis
For analysis of disease
Week 12
Flow cytometry analysis
For analysis of disease
Observe for survival Example 6: HDAC6 is Over Expressed in Human Primary B-CLL and Modulation of its Expression Alters Cell Viability in CLL Cell Lines Using RT-PCR analysis of twenty B-CLL with Rai stages ranging from 0-4, fifteen of twenty patients show elevated HDAC6 expression (FIG. 1A). Viability of CLL cell line Mec1 in this experiment was determined using MTS Cell-Titer 96® (Promega) analysis, and the results are shown in FIG. 1B. Two polyclonal HDAC6KD cells were developed by stably transfecting them with HDAC6 shRNA (Sigma-Plasmid NM_006044), and subsequently analyzed for viability and compared to non-targeted control counterpart (FIG. 1B—Left part). Mec1 cells were transfected with increasing concentrations of HDAC6 over-expressing (H6OE) plasmid following viability analysis. Next, Mec1 cells were treated with two HDAC6 inhibitors at various doses and assessed for viability by MTS (FIG. 1B—Right part).

Figure 2:
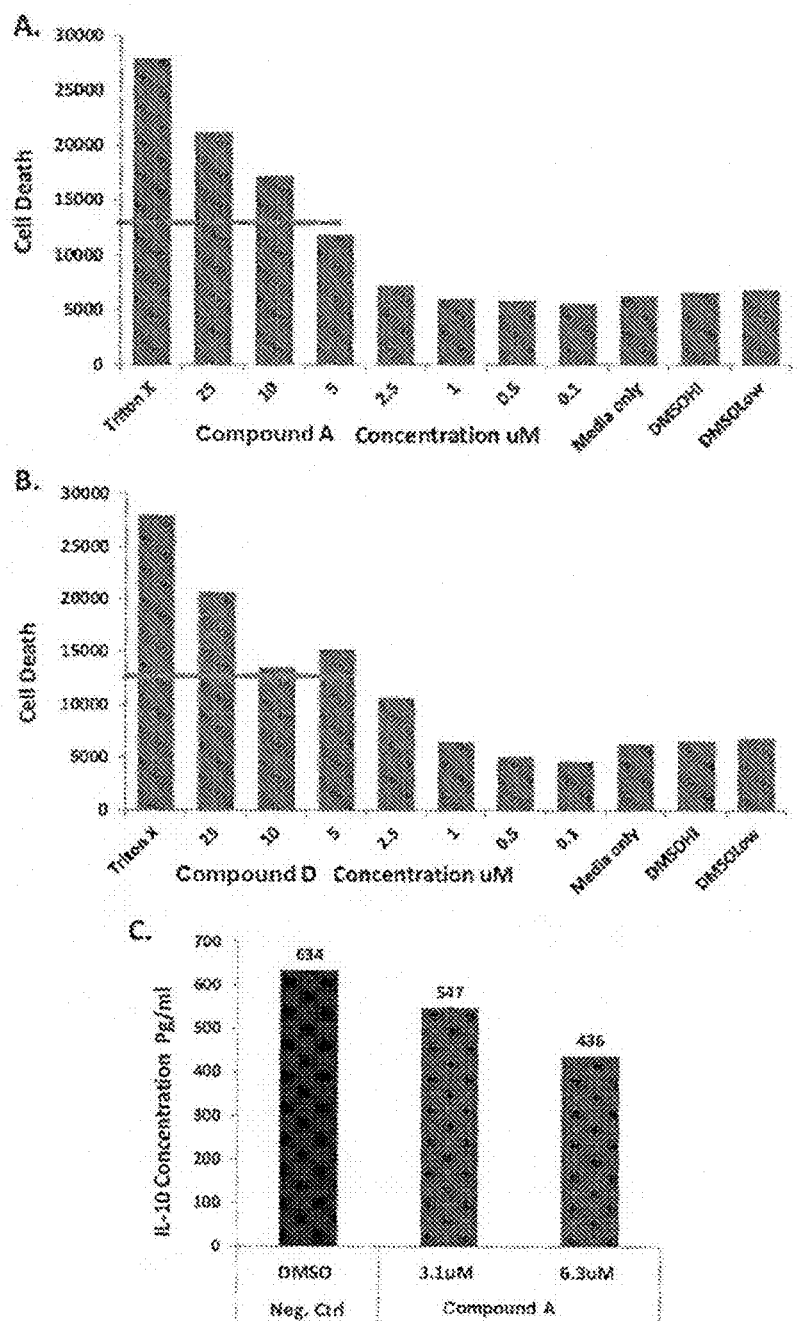
FIGS. 2A-2B show cell death measured using cellTox assay SyTox® Green (Promega) of OSU-CLL cells treated with Compound A (FIG. 2A) or Compound D (FIG. 2B) for 48 hours.
FIG. 2C shows production of IL-10 by Mec1 cells treated with Compound A for 24 hours and stimulated with LPS.

Example 7: Pharmacological Inhibition of HDAC6 Dose Dependently Decreases Expression of IL-10 and Reduces Viability in CLL Cell Lines OSU-CLL cells were treated with Compound A (FIG. 2A) or Compound D (FIG. 2B) for 48 hours and cells death was measured using cellTox assay SyTox® Green (Promega). Mec1 cells treated with Compound A for 24 hours and stimulated with LPS show a dose-dependent decrease in IL-10 production (important B cell survival factor) (FIG. 2C).

Figure 3:
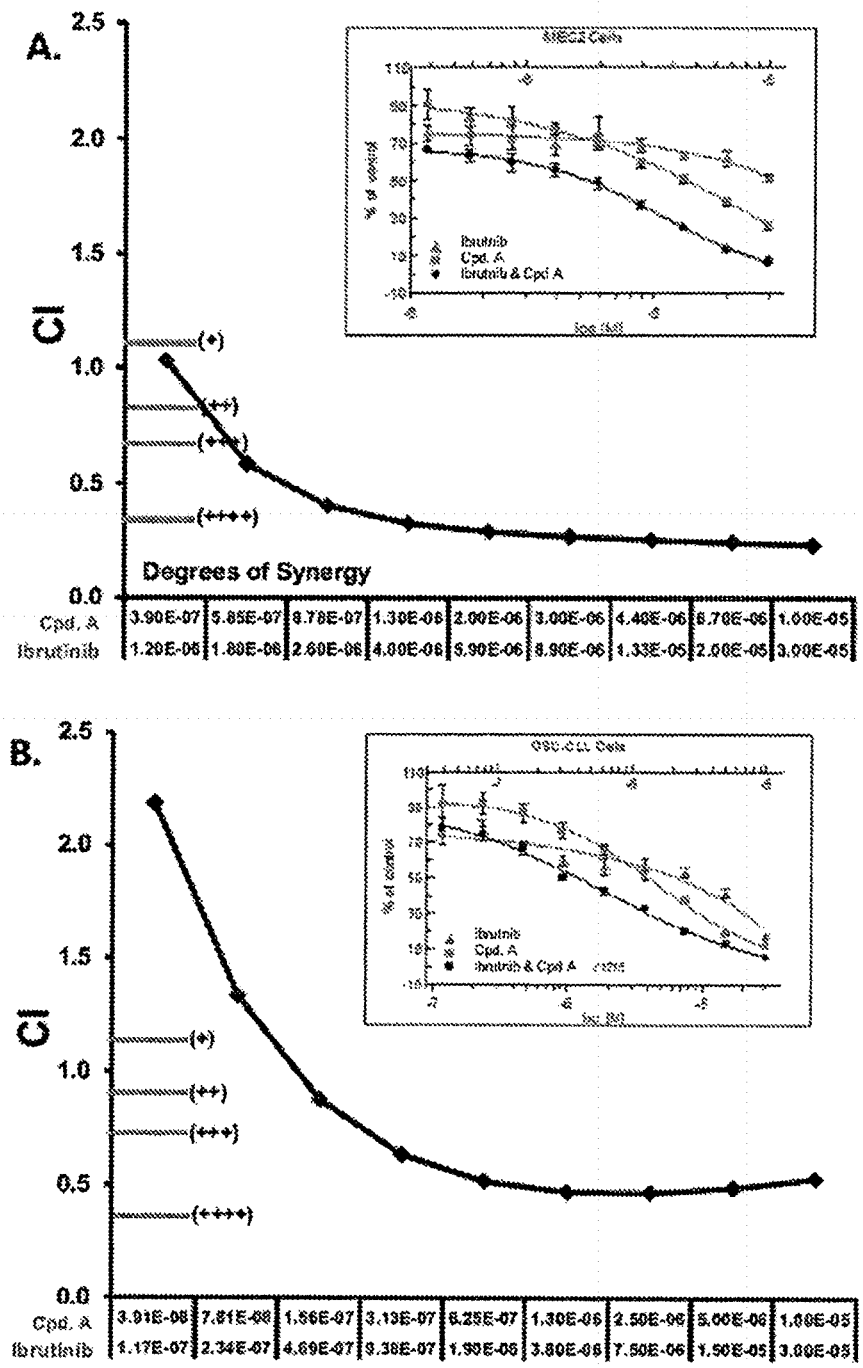
FIGS. 3A-3C show synergy plots of cell viability determined using the CellTiter-Blue (Promega) assay in Mec2 cells (FIG. 3A) and OSU-CLL (FIG. 3B) cells after a 72 hour treatment with Compound A and ibrutinib. The results were analyzed for synergism using the combination index (CI) method developed by Chou & Talalay (Chou T C, Cancer research 2010; 70(2): 440-6).
Figure 3:
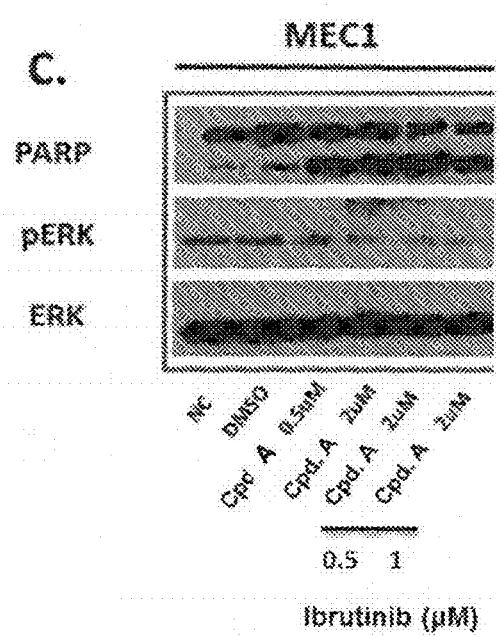

Example 8: Treatment of CLL Cell Lines with Compound A and Ibrutinib, Synergistically Decreases Viability and Alters BCR Signaling Pathway The activity of the combination of drugs was determined using the CellTiter-Blue (Promega) cell viability assay after a 72 hour treatment in Mec1 (FIG. 3A) and OSU-CLL (FIG. 3B) cells. The results were analyzed for synergism using the combination index (CI) method developed by Chou & Talalay (Chou T C. Cancer research 2010; 70(2): 440-6). Mec1 cells were treated with Compound A at varying doses (0.5 and 1 μM) alone or in combination with ibrutinib (0.2 and 1 μM) for 24 hrs. and blotted for PARP and pERK (FIG. 3C). These results demonstrate the synergistic effect of the combination of Compound A and ibrutinib on CLL cell viability.

Example 9: Biological or Pharmacological Manipulation of HDAC6 Reduces Disease Burden and Renders Survival Advantage Eight mice from eu-TCL1 and euTCL1/HDAC6KO groups were selected and aged up to 300 days (corresponding to the day the last euTCL1 expired) (FIG. 4A). euTCL1 mice succumbed to disease starting day 200 while ALL eu-TCL1/HDAC6KO mice survived (panel insert). Spleens from these mice were measured post-mortem and compared (p value<0.0005***) (FIG. 4A).

Eight C57BL/6 mice were adoptively transplanted with 5×10$^6$ splenocytes euTCL1 or euTCL1-HDAC6KO mice, n=4 per group). Mice injected with euTCL1/HDAC6KO splenocytes had a lower disease burden and survival advantage over euTCL1 splenocyte injected cohort (FIG. 4B).

Figure 4:
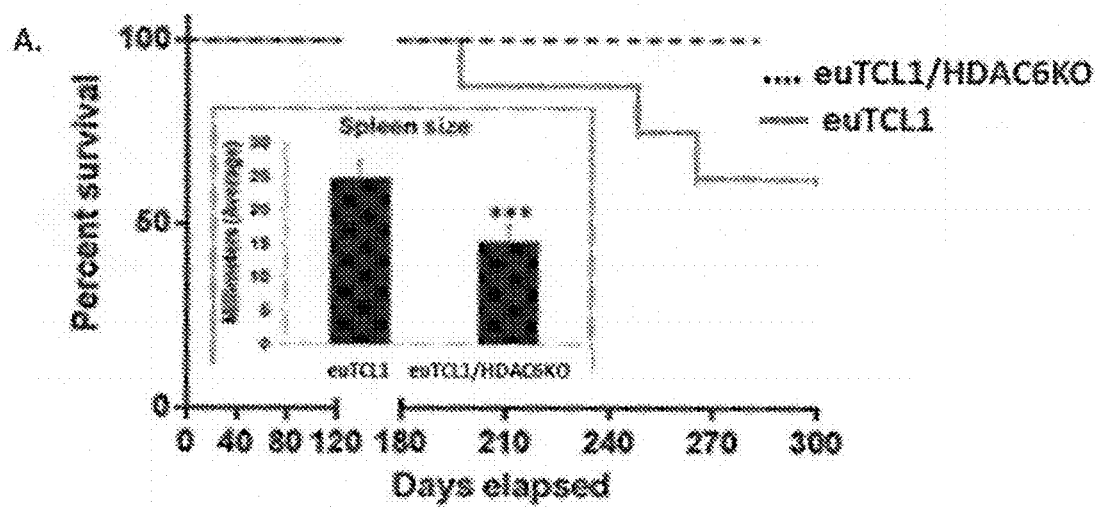
FIGS. 4A-4E show disease burden and survival advantage with biological or pharmacological manipulation of HDAC6.
Figure 4:
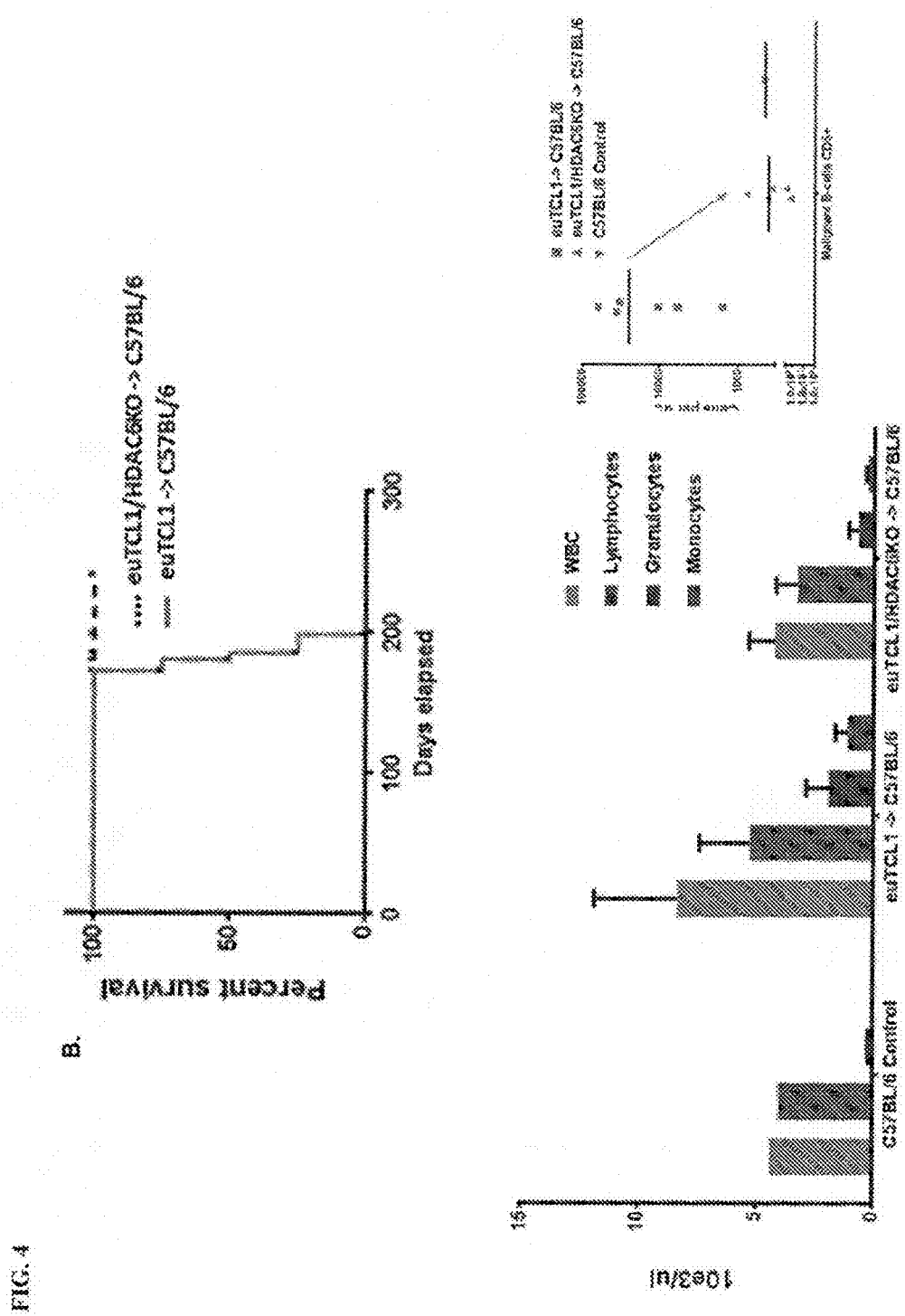
Figure 4:
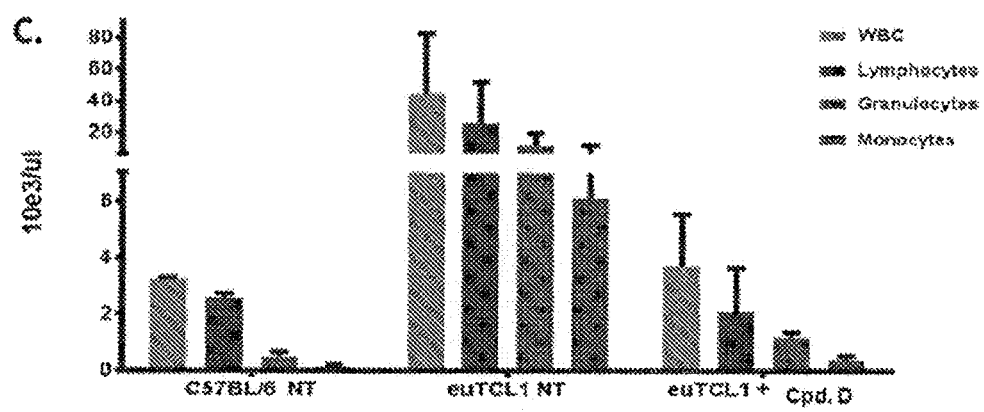
Figure 4:
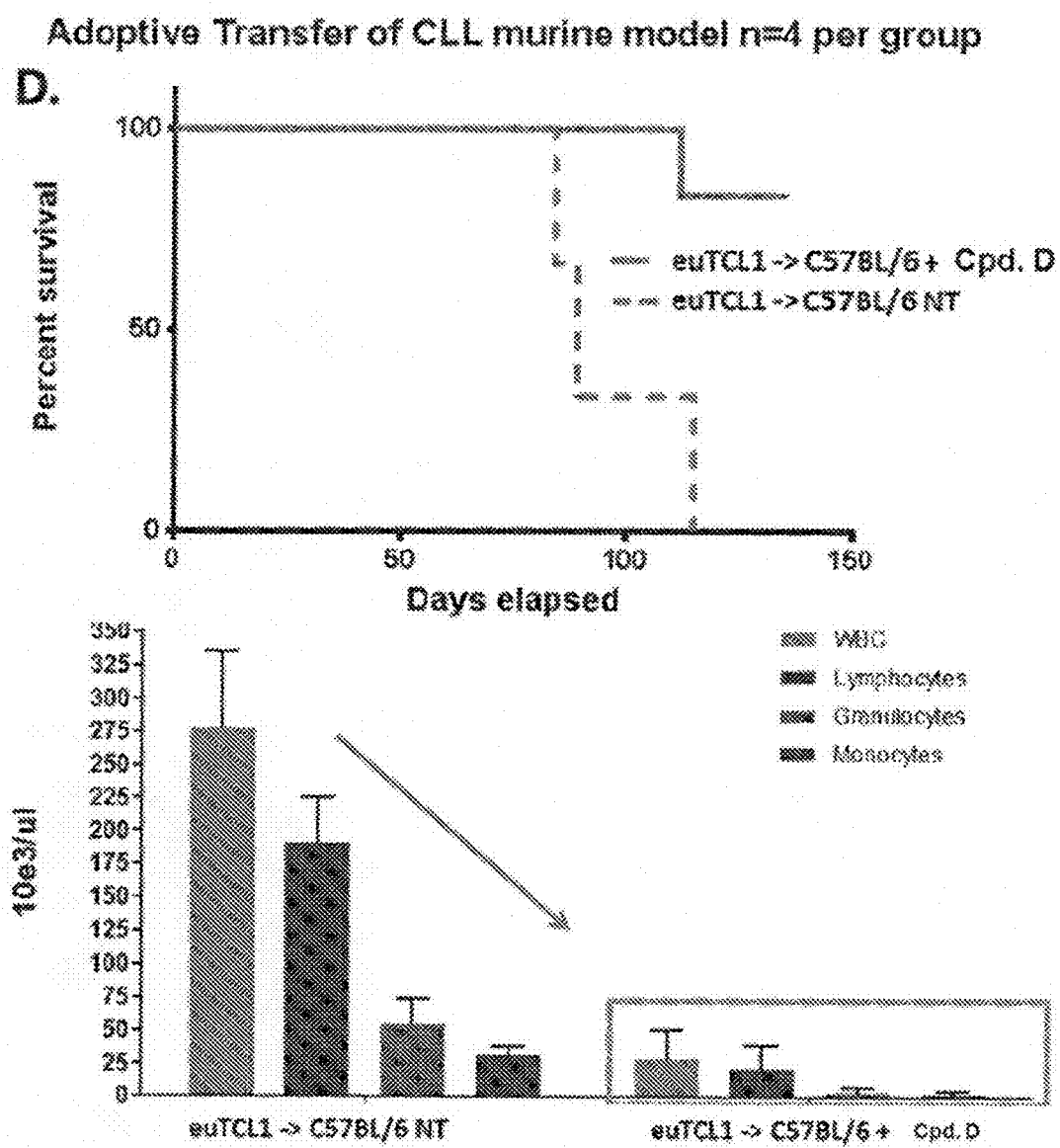
Figure 4:
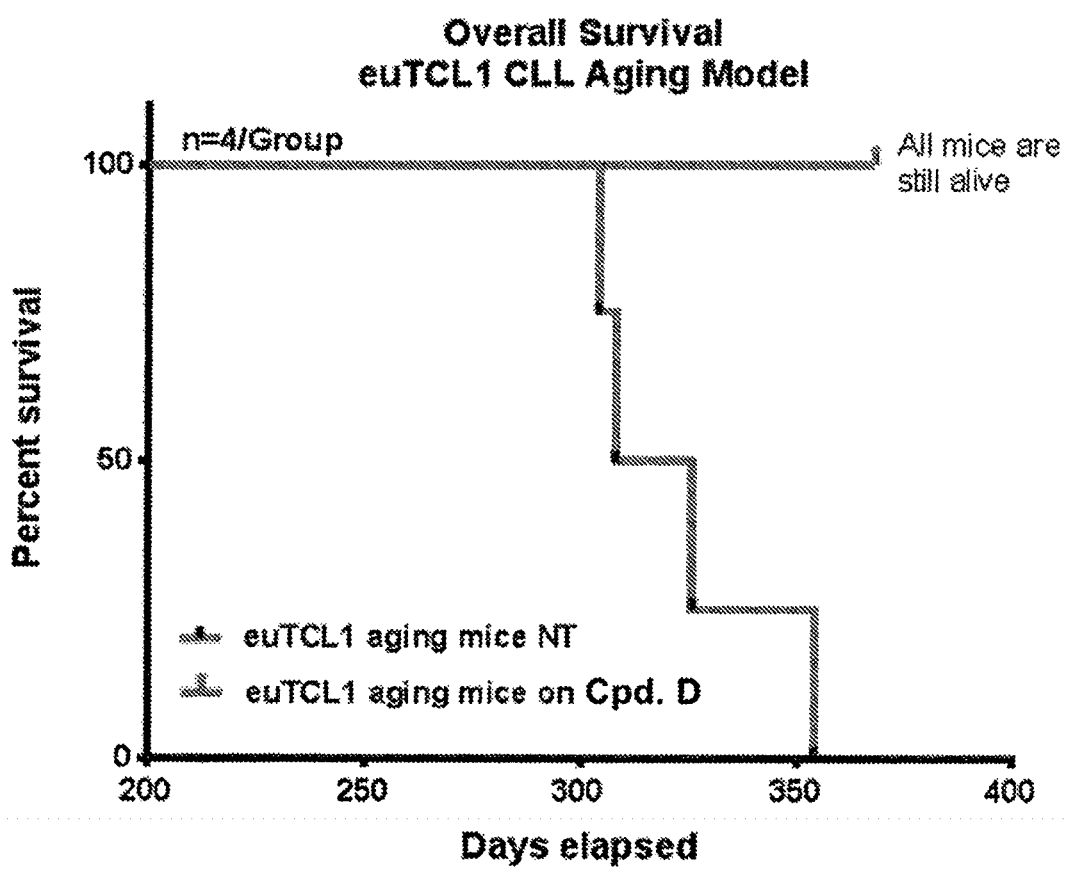

In an aging model of CLL, mice treated with Compound D showed significantly lower disease burden (9 months old/25 weeks post treatment start date) than mice treated without Compound D (FIG. 4C).

In an adoptive transfer experiments (FIG. 4D), mice receiving Compound D treatment have a more advantageous overall survival (Top of FIG. 4D) and significantly lower disease burden (Bottom of FIG. 4D).

In an aging model of CLL, mice treated with Compound D have a more advantageous overall survival than mice not treated with Compound D (FIG. 4E). As shown, at around day 350, all mice not treated with Compound D (NT) have succumbed to the disease.

Example 10: Inhibition of HDAC6 In Vivo and In Vitro Alters the Phenotypic Profile of B and T Cell Compartment in CLL Expression of PDL-1 and PDL-2 was reduced and the expression of MHC II was increased in HDAC6KD Mec1 cells when compared to non-target control counterpart (FIG. 5A).

Figure 5:
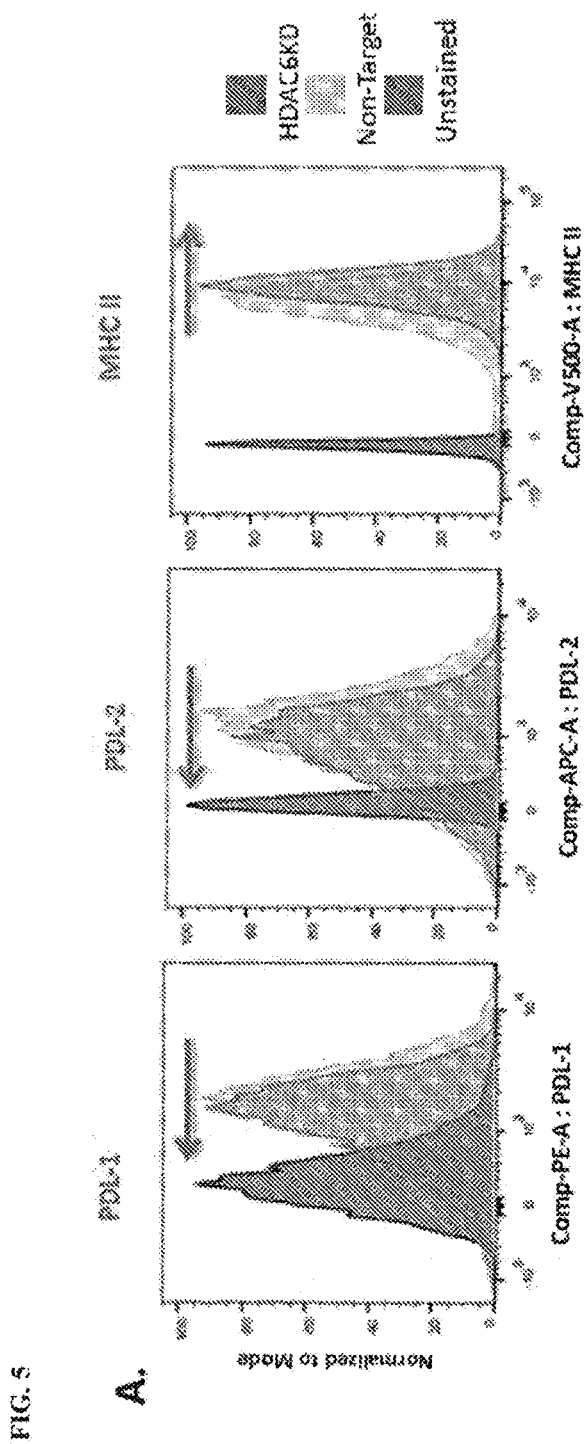
FIGS. 5A-5G show that inhibition of HDAC6 in vivo and in vitro alters the phenotypic profile of B- and T-cell compartment in CLL.
Figure 5:
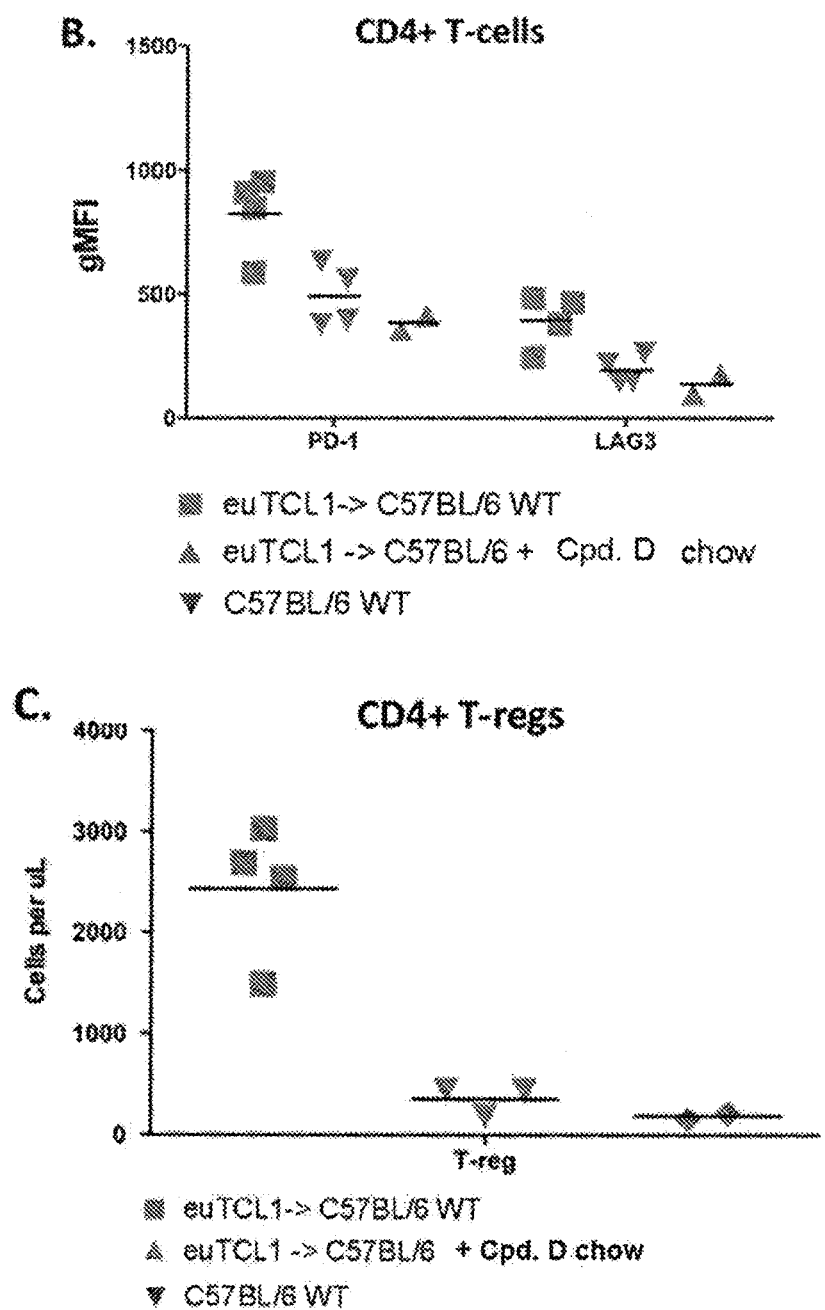
Figure 5:
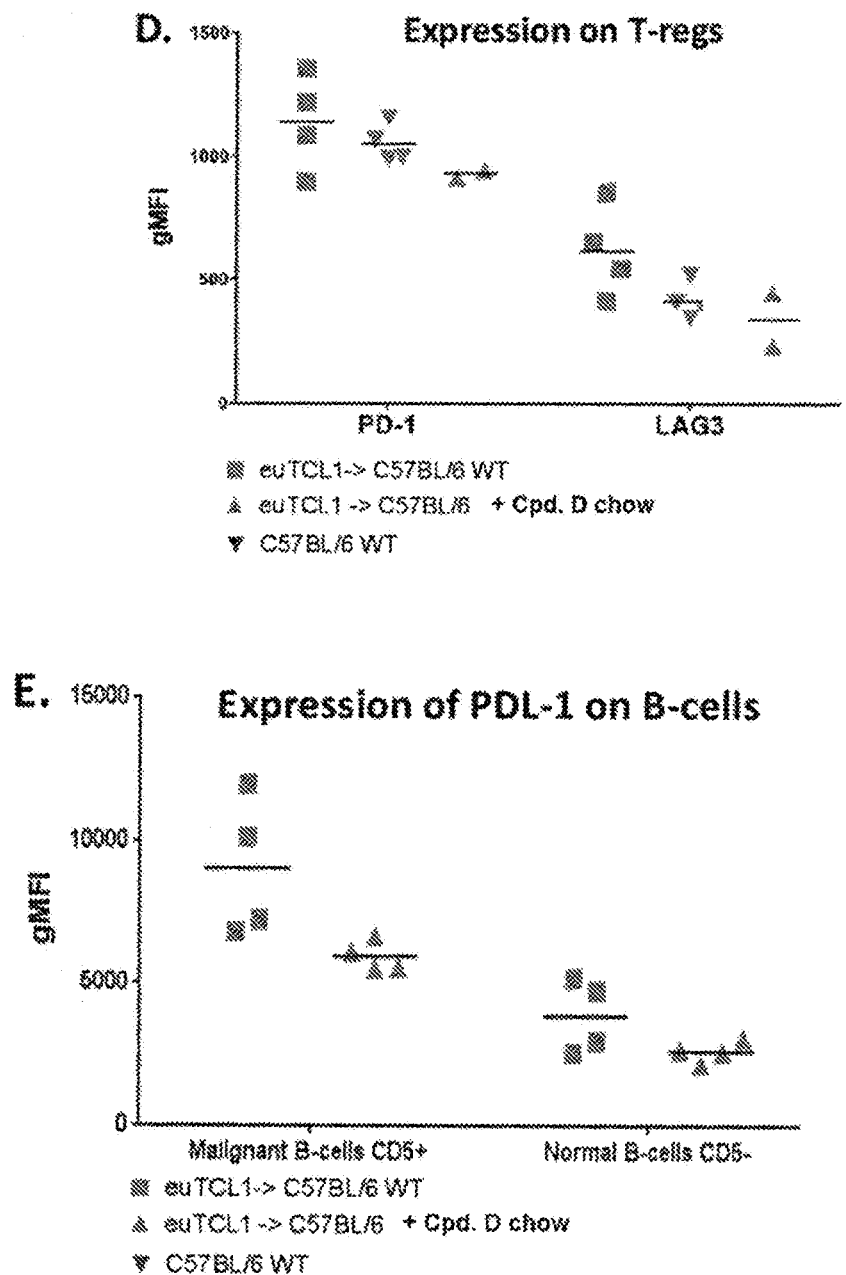
Figure 5:
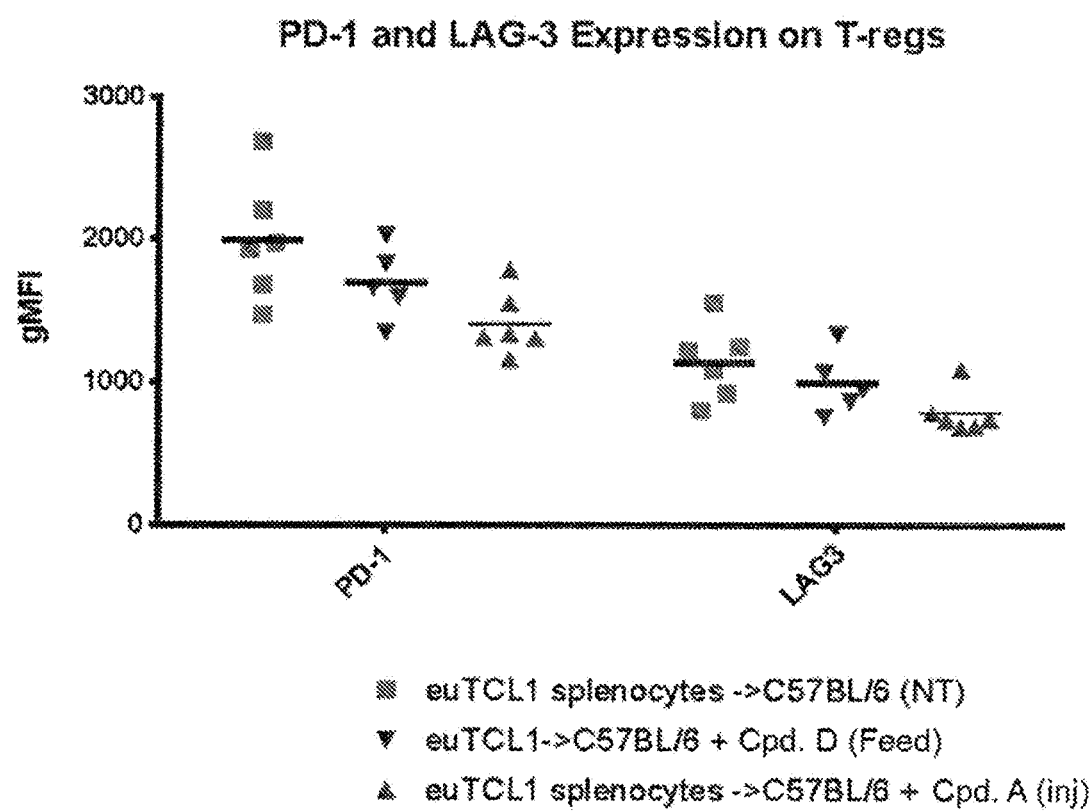
Figure 5:
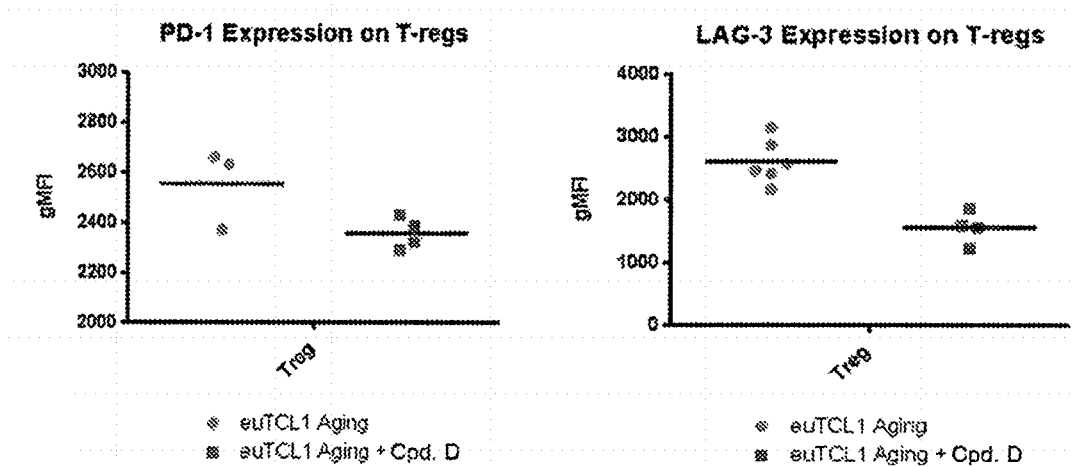

Flow cytometry analysis demonstrated normalization of PD-1 and LAG3 on CD4+ T-cells in mice receiving Compound D treatment in chow (week 10 post-adoptive transfer) (FIG. 5B).

Additionally, the number of T-regs (FIG. 5C), and the expression of PD-1 and LAG3 (FIG. 5D) molecules on these T-regs, appeared similar to those of a normal C57BL/6 WT mouse.

Expression of PD-L1 on B cells isolated from these treated mice with Compound D showed a decrease when compared to the non-treated animals (FIG. 5E).

Flow cytometry analysis and gating: B-cells (malignant population CD19+/CD5+/CD45R (B220)+/IgM+/Igk+; for normal B-cells CD19+/CD5−/CD45R (B220)+/IgM+/Igk− T-regs were identified as CD3+/CD4+/CD25 hi/IL-7R low. For Co-inhibitory molecule expression CD223 (LAG3), CD279 (PD-1), CD274 (PDL-1), and CD273 (PDL-2).

In adoptive transfer experiments, flow cytometry analysis demonstrated that the expression of PD-1 and LAG-3 was reduced in mice treated with Compound D feed, and in mice treated with Compound A by injection (FIG. 5F).

In an aging model of CLL, flow cytometry analysis demonstrated that the expression of PD-1 and LAG-3 on T-regs was reduced in mice treated with Compound D as compared to mice not treated with Compound D (FIG. 5G).

Figure 6:
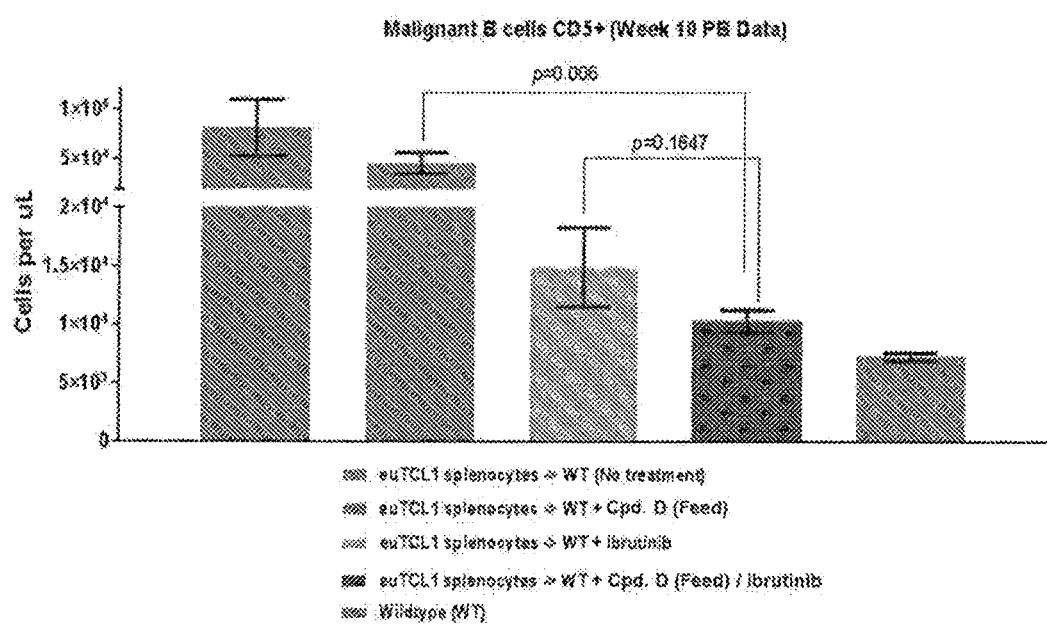
FIGS. 6A-6B show disease burden and survival advantage of mice treated with a combination of Compound D and Ibrutinib.
Figure 6:
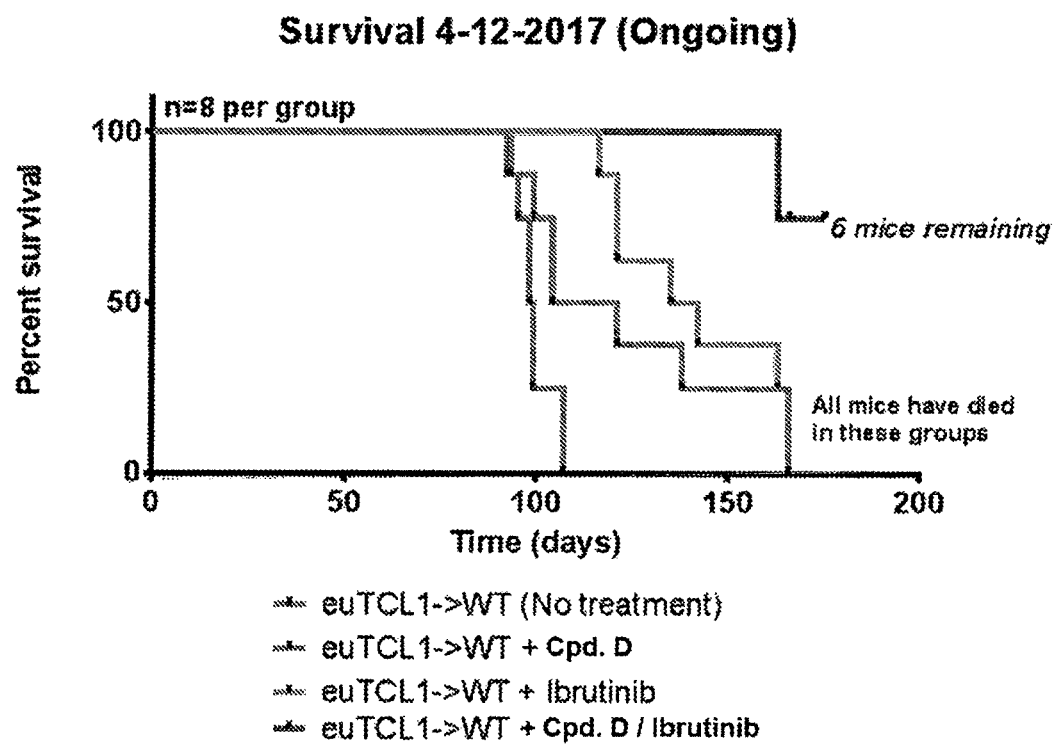

Example 11: The Combination of BTK Inhibitors and Compound D Causes Significantly Lower Disease Burden in a Mouse Model In adoptive transfer experiments, mice receiving a combination of Compound D and Ibrutinib demonstrated significantly lower disease burden (FIG. 6A). As shown, in the combinatorial treatment, using the adoptive transfer euTCL1 model receiving Ibrutinib in drinking water and Compound D in feed, a further decrease in tumor burden was found when compared to treatment with either compound alone. This observed effect on tumor burden occurred in conjunction with decreases in co-inhibitory molecules and circulating T-reg frequency. The combination was well tolerated and no significant toxicity was observed.

Also, mice receiving a combination of Compound D and Ibrutinib demonstrated significant advantageous overall survival when compared with mice receiving either Compound D or Ibrutinib alone (FIG. 6B). As shown, at the latest time point, all mice have succumbed to the disease except for the combination group.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:
1. A method for treating chronic lymphocytic leukemia in a subject in need thereof comprising administering to the subject a therapeutically effective amount of

(a) a histone deacetylase 6 (HDAC6) selective inhibitor, wherein the HDAC6 inhibitor is Compound B:

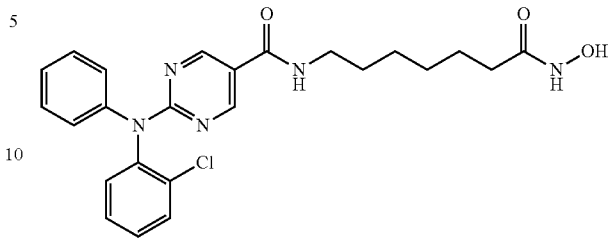

or a pharmaceutically acceptable salt thereof; and
(b) a Bruton's tyrosine kinase (BTK) inhibitor or a pharmaceutically acceptable salt thereof;
wherein the BTK inhibitor is ibrutinib or a pharmaceutically acceptable salt thereof;
the HDAC6 selective inhibitor and the BTK inhibitor are each administered in a sub-therapeutically effective amount;
the HDAC6 selective inhibitor and the BTK inhibitor reduce the expression of an inhibitory checkpoint molecule in a T- and/or B-cell compartment in the subject;
wherein the checkpoint molecule is selected from the group consisting of CD274 (PDL-1), CD273 (PDL-2), CD80 (87-1), CD86 (B7-2), CD 152 (CTLA4), CD275 (B7RP1), CD276 (B7-H3), B7-H4 (VTCN1), CD270 (HVEM), BLTA, GAL9, CD366 (TIMS), A2aR, CD279 (PD-1), KIR, and CD223 (LAGS); and
the ratio of Compound B to the BTK inhibitor is 3:1.
2. The method of claim 1, wherein the HDAC6 selective inhibitor and the BTK inhibitor are in the same formulation.
3. The method of claim 1, wherein the HDAC6 selective inhibitor and the BTK inhibitor are in separate formulations.
4. The method of claim 1, wherein the HDAC6 selective inhibitor and the BTK inhibitor are administered at the same time.
5. The method of claim 1, wherein the HDAC6 selective inhibitor and the BTK inhibitor are administered at different times.
6. The method of claim 1, wherein checkpoint molecules are CD274 (PDL-1) and CD273 (PDL-2).
7. The method of claim 1, wherein the checkpoint molecule is reduced on regulatory T lymphocytes (Tregs).
8. The method of claim 7, wherein the T lymphocytes are CD4+ or CD8+.

* * * * *